(12) United States Patent
Nagano et al.

(10) Patent No.: US 12,401,884 B2
(45) Date of Patent: Aug. 26, 2025

(54) INFORMATION PROCESSING DEVICE, INFORMATION PROCESSING METHOD, AND PROGRAM

(71) Applicant: SONY GROUP CORPORATION, Tokyo (JP)

(72) Inventors: Hidetoshi Nagano, Tokyo (JP); Kazuhiro Shimauchi, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 104 days.

(21) Appl. No.: 18/557,685

(22) PCT Filed: Jan. 28, 2022

(86) PCT No.: PCT/JP2022/003240
§ 371 (c)(1),
(2) Date: Oct. 27, 2023

(87) PCT Pub. No.: WO2022/244314
PCT Pub. Date: Nov. 24, 2022

(65) Prior Publication Data
US 2024/0223883 A1    Jul. 4, 2024

(30) Foreign Application Priority Data

May 21, 2021    (JP) .................................. 2021-086376

(51) Int. Cl.
*H04N 23/611*    (2023.01)
*A61B 5/11*    (2006.01)
(Continued)

(52) U.S. Cl.
CPC .......... *H04N 23/611* (2023.01); *A61B 5/1116* (2013.01); *H04N 5/268* (2013.01);
(Continued)

(58) Field of Classification Search
CPC ...... H04N 23/611; H04N 5/268; H04N 23/64; H04N 23/667; H04N 23/69; H04N 23/60;
(Continued)

(56) References Cited

U.S. PATENT DOCUMENTS

| | | | | |
|---|---|---|---|---|
| 2013/0342720 A1* | 12/2013 | Azami | ................... | H04N 7/183 |
| | | | | 348/222.1 |
| 2017/0318224 A1* | 11/2017 | Kuchiki | ............... | H04N 23/681 |
| 2023/0215038 A1* | 7/2023 | Shimauchi | .............. | G06T 7/246 |
| | | | | 382/103 |

FOREIGN PATENT DOCUMENTS

| | | |
|---|---|---|
| JP | 2007-067510 A | 3/2007 |
| JP | 2010-081246 A | 4/2010 |

(Continued)

OTHER PUBLICATIONS

International Search Report and Written Opinion of PCT Application No. PCT/JP2022/003240, issued on Mar. 22, 2022, 08 pages of ISRWO.

*Primary Examiner* — Christopher K Peterson
(74) *Attorney, Agent, or Firm* — CHIP LAW GROUP

(57) ABSTRACT

An information processing device (10) includes a target composition calculation unit (16) and a composition transition determination unit (17). The target composition calculation unit (16) calculates a target composition based on a state of a subject. The composition transition determination unit (17) switches a transition mode for transition to the target composition between a smooth composition transition mode and an instantaneous composition transition mode based on a situation of a change in state of the subject. The smooth composition transition mode is a transition mode in which a composition gradually transitions to the target composition. The instantaneous composition transition
(Continued)

mode is a transition mode in which the composition instantaneously transitions to the target composition.

17 Claims, 26 Drawing Sheets

(51) Int. Cl.
  *H04N 5/268* (2006.01)
  *H04N 23/60* (2023.01)
  *H04N 23/667* (2023.01)
  *H04N 23/69* (2023.01)
(52) U.S. Cl.
  CPC ............ *H04N 23/64* (2023.01); *H04N 23/667* (2023.01); *H04N 23/69* (2023.01); *A61B 2503/12* (2013.01)
(58) Field of Classification Search
  CPC ... A61B 5/1116; A61B 2503/12; G03B 15/00; G03B 17/00; G03B 17/56
  See application file for complete search history.

(56) References Cited

FOREIGN PATENT DOCUMENTS

| | | |
|---|---|---|
| JP | 2014-007653 A | 1/2014 |
| JP | 2016-158241 A | 9/2016 |
| JP | 2017-063340 A | 3/2017 |
| JP | 2019-191736 A | 10/2019 |

\* cited by examiner

FIG.1
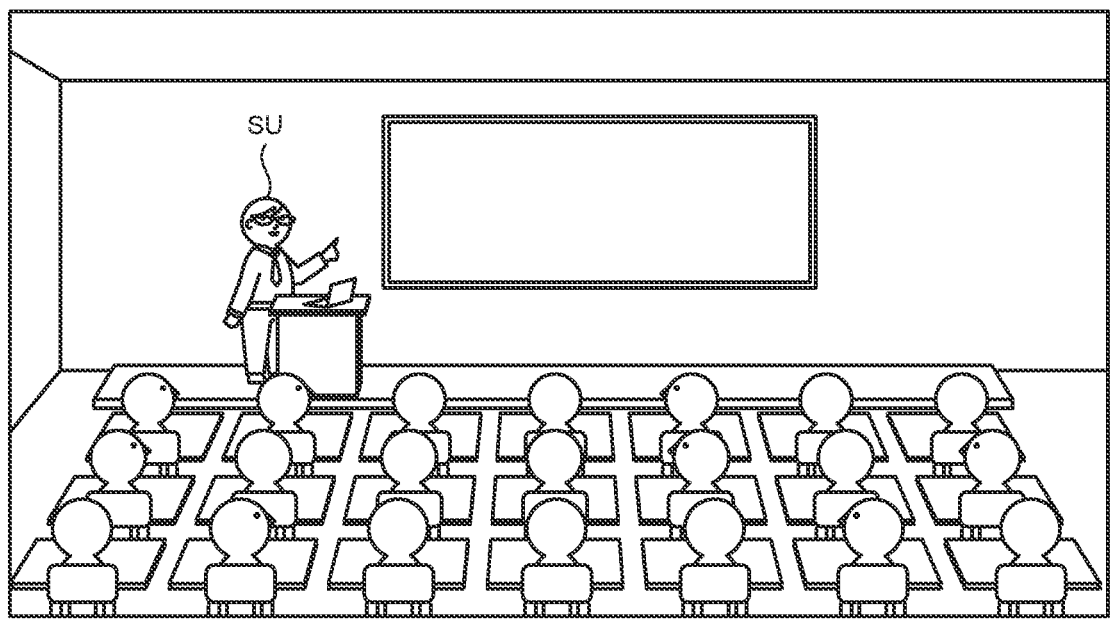
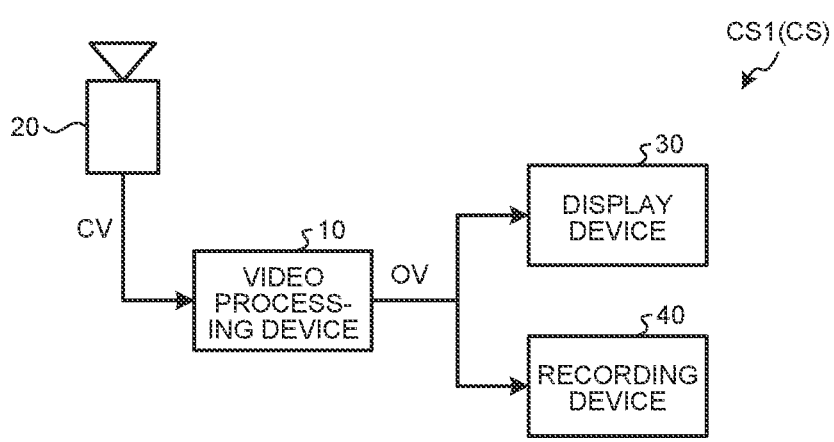

FIG.20
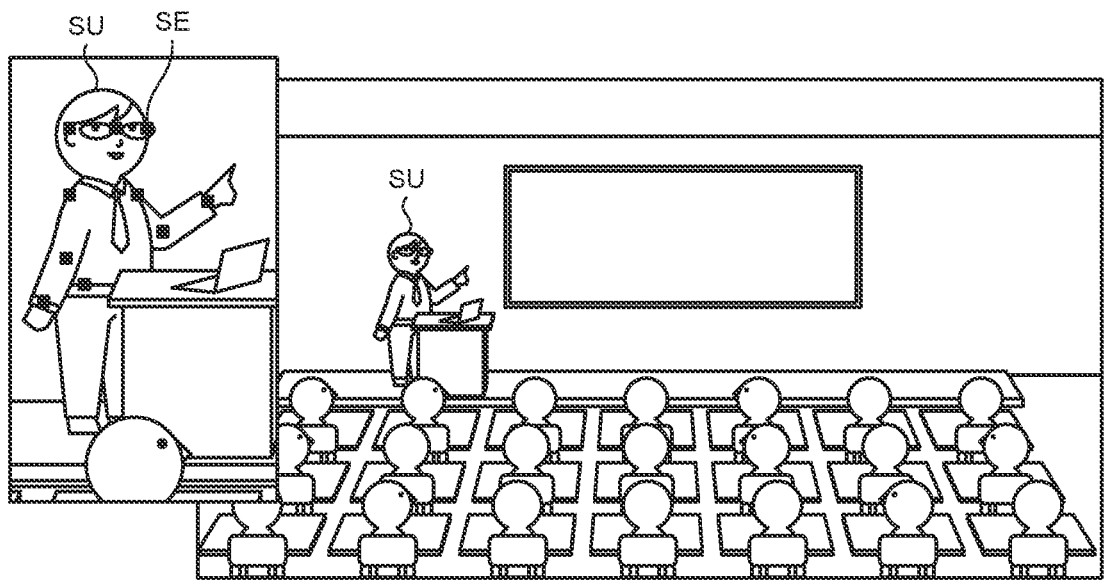
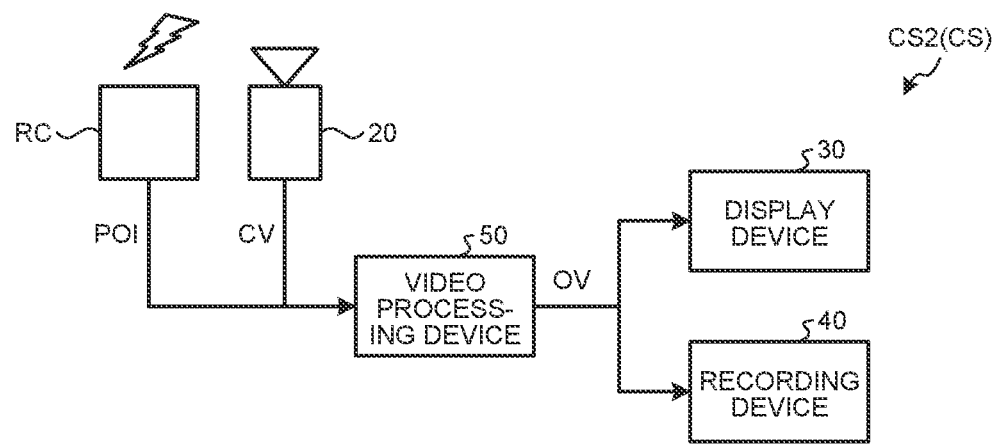

INFORMATION PROCESSING DEVICE, INFORMATION PROCESSING METHOD, AND PROGRAM

CROSS REFERENCE TO RELATED APPLICATIONS

This application is a U.S. National Phase of International Patent Application No. PCT/JP2022/003240 filed on Jan. 28, 2022, which claims priority benefit of Japanese Patent Application No. JP 2021-086376 filed in the Japan Patent Office on May 21, 2021. Each of the above-referenced applications is hereby incorporated herein by reference in its entirety.

FIELD

The present invention relates to an information processing device, an information processing method, and a program.

BACKGROUND

In the field of a lecture capture or the like, a technology for automatically imaging a subject (for example, a lecturer) has been proposed. In the automatic imaging, the subject is tracked, and framing is performed in accordance with the position of the subject. When the framing is performed, it is important to determine a composition and appropriately transition the composition. For example, in a case where the subject faces the right or moves to the right, a composition in which a space is left on the right side of the subject is desirable.

However, states such as a movement direction and an orientation are not always the same. For example, the subject is not always facing the right, but changes its orientation. In addition, a timing of changing the orientation also changes from time to time, and the orientation may change frequently depending on contents of a lecture or communication with students.

CITATION LIST

Patent Literature

Patent Literature 1: JP 2019-191736 A
Patent Literature 2: JP 2010-081246 A
Patent Literature 3: JP 2016-158241 A
Patent Literature 4: JP 2017-063340 A

SUMMARY

Technical Problem

Since an automatic imaging result is a moving image, a composition that has been desirable so far becomes no more desirable at a moment when the state (for example, the movement direction or the orientation of the subject) of the subject changes. For this reason, it is necessary to adjust the current composition with a desirable composition after the state of the subject changes as a target composition, but unnatural composition adjustment is performed in some cases.

For example, Patent Literature 1 discloses a technology for determining the orientation of the subject. However, in Patent Literature 1, since framing is not intended, even if the orientation of the subject obtained here is applied as it is, appropriate framing as described above is not achieved. For example, in Patent Literature 1, the orientation of the subject is determined using a direction of a hand, but the direction in which the hand is spread does not necessarily coincide with the orientation of the subject. Furthermore, consideration is not made to appropriately capture continuity or change in orientation of the subject in a time direction.

Examples of technologies related to the framing include Patent Literature 2, Patent Literature 3, and Patent Literature 4. In any case, a direction of a line of sight and the like are determined, and devising of a composition in which a space is left in the direction is made. However, how to capture a change in direction of the line of sight or the like in the time direction and apply the change to the framing is not considered.

Therefore, the present disclosure proposes an information processing device, an information processing method, and a program capable of setting an appropriate composition according to a change in state of a subject.

Solution to Problem

According to the present disclosure, an information processing device is provided that comprises: a target composition calculation unit that calculates a target composition based on a state of a subject; and a composition transition determination unit that switches a transition mode for transition to the target composition between a smooth composition transition mode in which the composition gradually transitions to the target composition and an instantaneous composition transition mode in which the composition instantaneously transitions to the target composition based on a situation of a change in the state. According to the present disclosure, an information processing method in which an information process of the information processing device is executed by a computer, and a program causing a computer to perform the information process of the information processing device are provided.

BRIEF DESCRIPTION OF DRAWINGS

FIG. 1 is a diagram illustrating an imaging system according to a first embodiment.

FIG. 20 is a diagram illustrating an imaging system according to a second embodiment.

DESCRIPTION OF EMBODIMENTS

Figure 2:
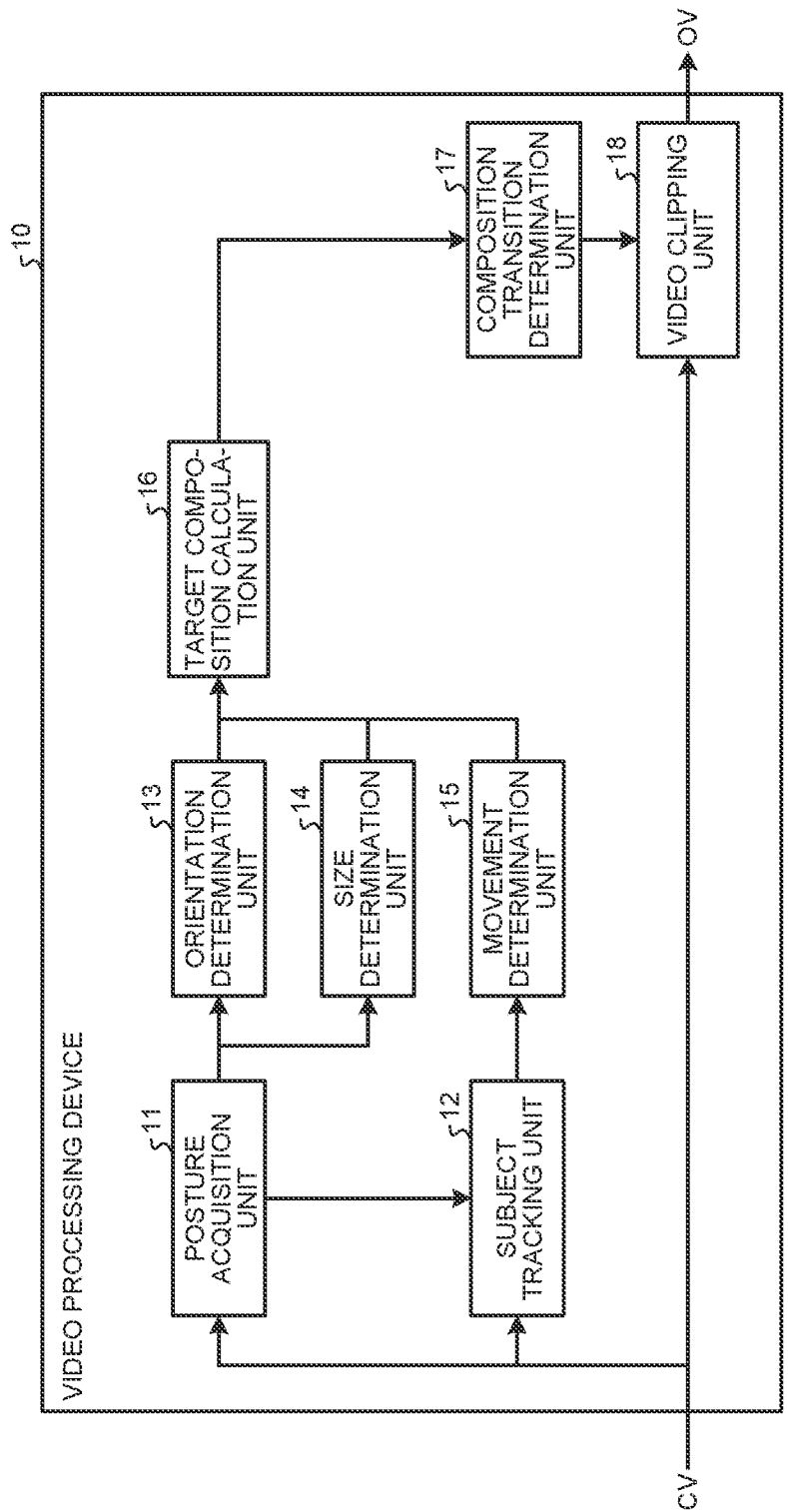
FIG. 2 is a block diagram illustrating a functional configuration of a video processing device.

Hereinafter, embodiments of the present disclosure will be described in detail with reference to the drawings. In each of the following embodiments, the same reference signs denote the same portions, and an overlapping description will be omitted.

The description will be made in the following order.
[1. First Embodiment]
[1-1. Configuration of Imaging System]
[1-2. Video Processing Method]
[1-2-1. Posture Acquisition Unit]
[1-2-2. Subject Tracking Unit]
[1-2-3. Orientation Determination Unit]
[1-2-4. Size Determination Unit]
[1-2-5. Movement Determination Unit]
[1-2-6. Target Composition Calculation Unit]
[1-2-7. Composition Transition Determination Unit]
[1-2-8. Video Clipping Unit]
[1-3. Effects]
[2. Second Embodiment]
[3. Third Embodiment]
[3-1. Configuration of Imaging System]
[3-2. Configuration of Video Switcher]
[3-3. Video Processing Method]
[3-4. Effects]
[4. Fourth Embodiment]
[5. Fifth Embodiment]
[5-1. Functional Configuration of Video Processing Device]
[5-2. Video Processing Method]
[5-3. Effects]
[6. First Modified Example]
[7. Second Modified Example]
[8. Third Modified Example]
[9. Hardware Configuration Example of Imaging System]

1. First Embodiment 1-1. Configuration of Imaging System

Hereinafter, an example of a configuration of an imaging system CS will be described with reference to the drawings. FIG. 1 is a diagram illustrating an imaging system CS1 according to a first embodiment.

The imaging system CS1 is a system that performs a lecture capture (lecture recording). The imaging system CS1 automatically tracks a lecturer who is a subject SU and automatically records a lecture content. For example, the imaging system CS1 includes a video processing device 10, a camera 20, a display device 30, and a recording device 40.

The camera 20 can image a range in which the subject SU moves around. The video processing device 10 performs framing on a captured video CV captured by the camera 20. The framing refers to processing of clipping a video area corresponding to a composition from the captured video CV. Since the processing is similar to work of adjusting an angle of view, a video area to be clipped is referred to as an angle AV of view (see FIG. 9) in the following description.

The composition means a configuration related to a position and size of the subject SU appearing in the video. For example, according to the rule of thirds, a screen is divided into three in each of vertical and horizontal directions, and the subject SU is arranged at a point where division lines DL (see FIG. 15) intersect each other. When the subject SU faces the right, a composition in which the subject SU is arranged on the left division line DL (a lead room is provided on the right side of the subject SU) is adopted. When the subject SU faces the left, a composition in which the subject SU is arranged on the right division line DL (a lead room is provided on the left side of the subject SU) is adopted. As for the size of the subject SU, compositions such as a long shot, a full figure, a knee shot, a waist shot, a bust shot, and a close-up according to an imaging range of the subject SU are known.

The video processing device 10 determines a target composition based on a state of the subject SU. For example, the video processing device 10 stores a plurality of types of compositions in which the positions or sizes of the subject SU are different as standard compositions. The video processing device 10 selects, as the target composition, a specific type of composition according to the state of the subject SU.

For example, when the subject SU is giving a lecture while facing the right side, the video processing device 10 arranges the subject SU on the division line DL on the left side of the screen, and determines, as the target composition, a composition for framing the subject SU in a bust shot. When the subject SU is moving to the left side, the video processing device 10 arranges the subject SU on the division line DL on the right side of the screen, and determines, as the target composition, a composition for framing the subject SU in a full figure. The state of the subject SU is acquired, for example, by performing image analysis on the captured video CV of the subject SU.

The video processing device 10 determines the next composition based on the current composition and a target composition TCP. The video processing device 10 generates angle-of-view information indicating a position and a size of the angle AV of view (a video area to be clipped) based on the determined composition. The video processing device 10 clips the video area based on the angle-of-view information. The video processing device 10 outputs the video area clipped from the captured video CV as a framing video OV.

The display device 30 displays the framing video OV output from the video processing device 10. The recording device 40 records the framing video OV. The respective devices included in the imaging system CS1 may be directly connected via a high-definition multimedia interface (HDMI (registered trademark)), a serial digital interface (SDI), or the like, or may be connected via a wired or wireless network.

1-2. Video Processing Method

FIG. 2 is a block diagram illustrating a functional configuration of the video processing device 10.

The video processing device 10 is an information processing device that processes various types of information. The video processing device 10 includes a posture acquisition unit 11, a subject tracking unit 12, an orientation determination unit 13, a size determination unit 14, a movement determination unit 15, a target composition calculation unit 16, a composition transition determination unit 17, and a video clipping unit 18.

Figure 3:
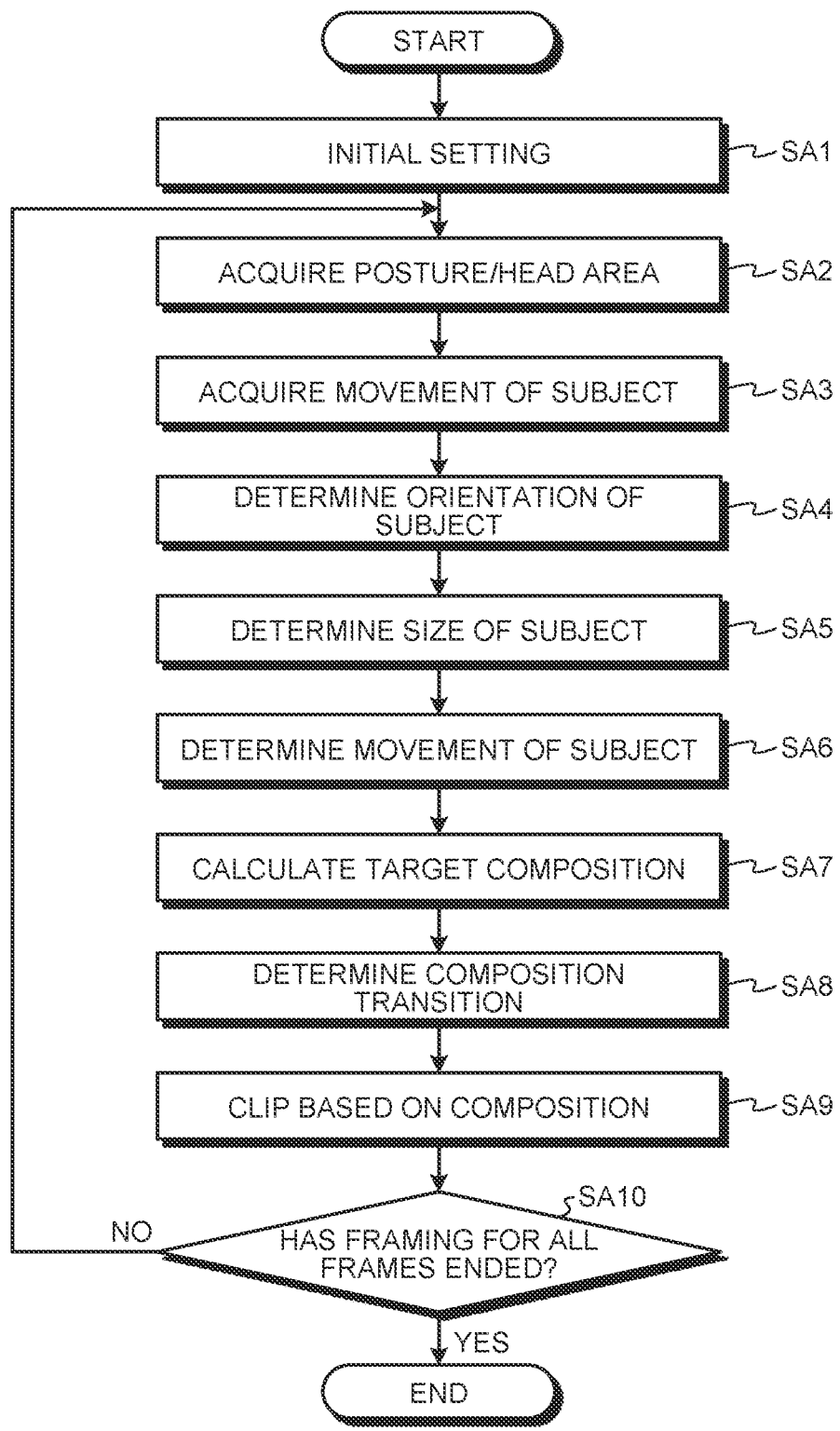
FIG. 3 is a flowchart illustrating a flow of entire video processing.

FIG. 3 is a flowchart illustrating a flow of entire video processing.

After performing initial setting of a state of a counter or the like necessary for processing (step SA1), the posture acquisition unit 11 of the video processing device 10 acquires the posture of the subject SU and a head area HEA (see FIG. 14) (step SA2). Next, the subject tracking unit 12 of the video processing device 10 acquires movement of the subject SU by matching with the previous frame or the like (step SA3). The orientation determination unit 13, the size determination unit 14, and the movement determination unit 15 of the video processing device 10 determine the orientation of the subject SU, the size of the subject SU, and the movement of the subject SU, respectively, based on the acquired information (steps SA4, SA5, and SA6).

The target composition calculation unit 16 of the video processing device 10 calculates the target composition TCP (see FIG. 15) suitable for an input frame based on the determination result (step SA7).

Subsequently, the composition transition determination unit 17 of the video processing device 10 determines transition from a current composition CP (see FIG. 15) to the target composition TCP, and determines the composition CP for the input frame (step SA8). The video clipping unit 18 clips and outputs the framing video OV based on the determined composition CP (step SA9).

The video processing device 10 determines whether or not framing has been performed for all frames (step SA10). In a case where there is a next frame (step SA10: no), the processing returns to step SA2, and the above-described processing is repeated until framing is performed for all the frames. In a case where there is no next frame (step SA10: yes), the video processing device 10 ends the processing.
[1-2-1. Posture Acquisition Unit]

Figure 4:
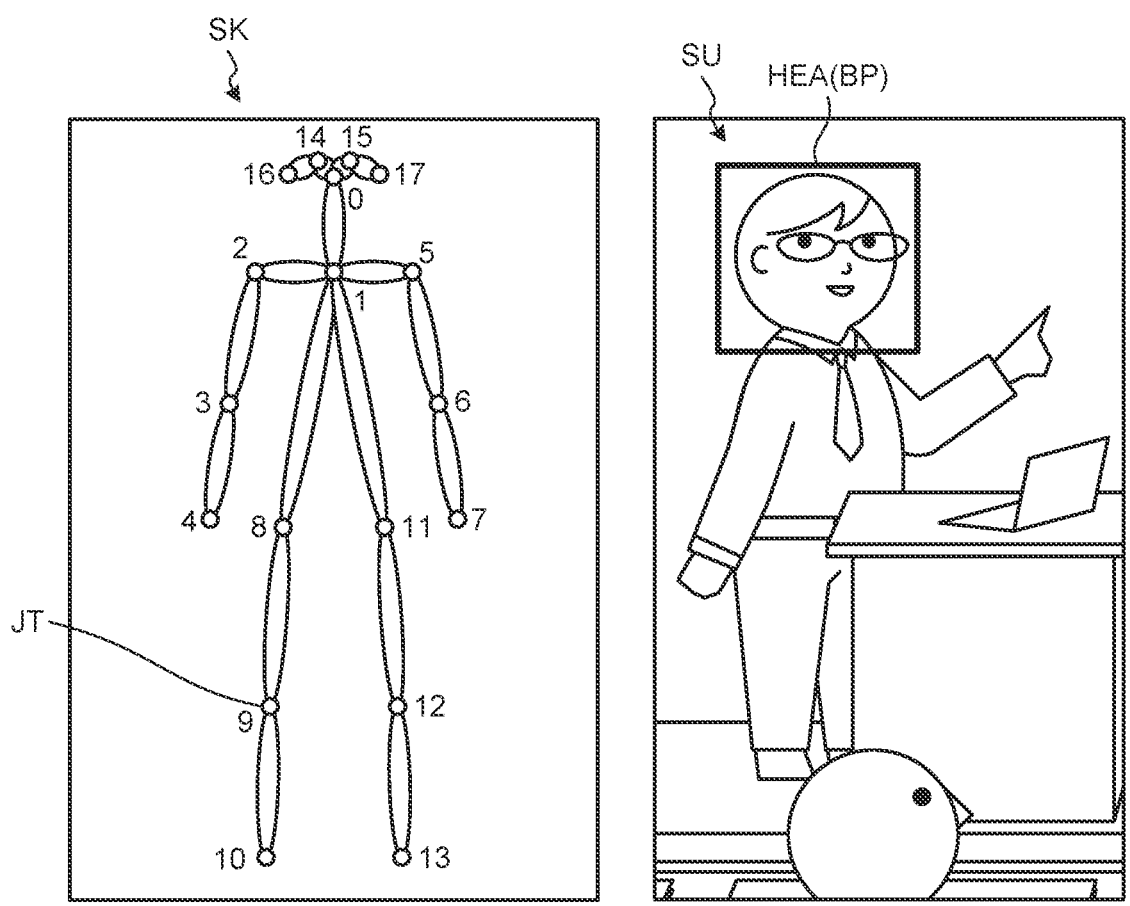
FIG. 4 is a view illustrating an example of posture information acquired by a posture acquisition unit.

FIG. 4 is a view illustrating an example of posture information acquired by the posture acquisition unit 11.

The posture acquisition unit 11 acquires a body part BP to be used by the orientation determination unit 13 and the size determination unit 14 from the captured video CV by image analysis processing. The posture acquisition unit 11 extracts the posture information of the subject SU by analyzing an image of the body part BP.

For example, skeleton data SK as illustrated on the left side of FIG. 4 can be extracted from the captured video CV by using a deep learning technology, and positions of face parts and joints JT such as the neck, the shoulder, the elbow, the wrist, the waist, the knee, and the ankle can be acquired. The position of the joint JT can be used as a part of the posture information. In addition, there is also an image processing method of estimating the head area HEA as illustrated on the right side of FIG. 4 by using the deep learning technology. The head area HEA can also be used as a part of the posture information. The position of the joint JT and the head area HEA may be obtained by separate estimation processings or may be obtained by one estimation processing.
[1-2-2. Subject Tracking Unit]

The subject tracking unit 12 detects movement of the subject SU between frames. For this, it is possible to use movement amount calculation processing in which an image is directly input, such as optical flow processing of performing matching for each pixel, and movement amount calculation processing based on data obtained by processing an image once, such as matching processing between frames of the body part BP obtained by the posture acquisition unit 11. In order to improve robustness, movement amount calculation can be performed using both the image and the matching of the body part BP.
[1-2-3. Orientation Determination Unit]

Figure 5:
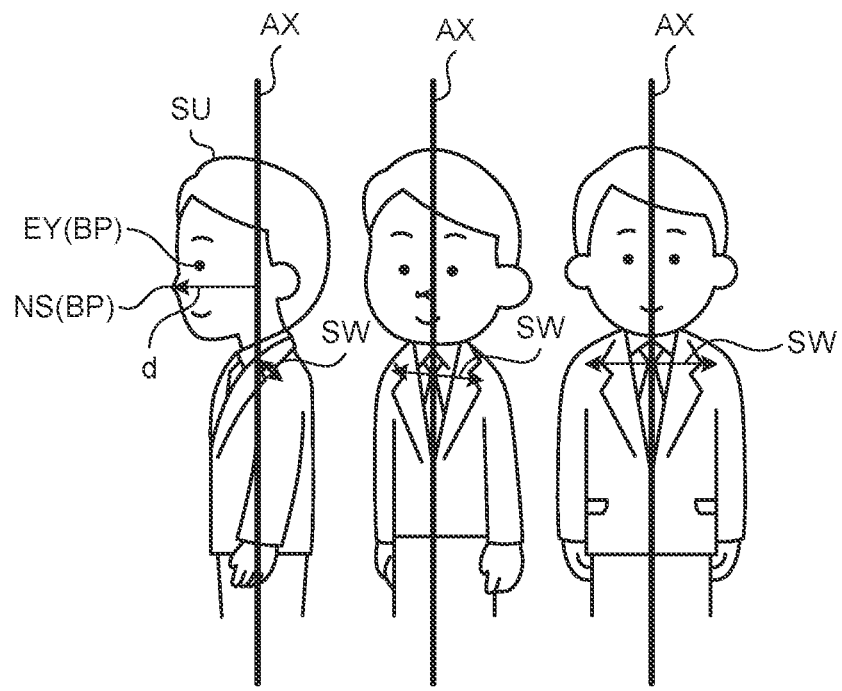
FIG. 5 is a view for describing a method of determining an orientation of a subject.
Figure 6:
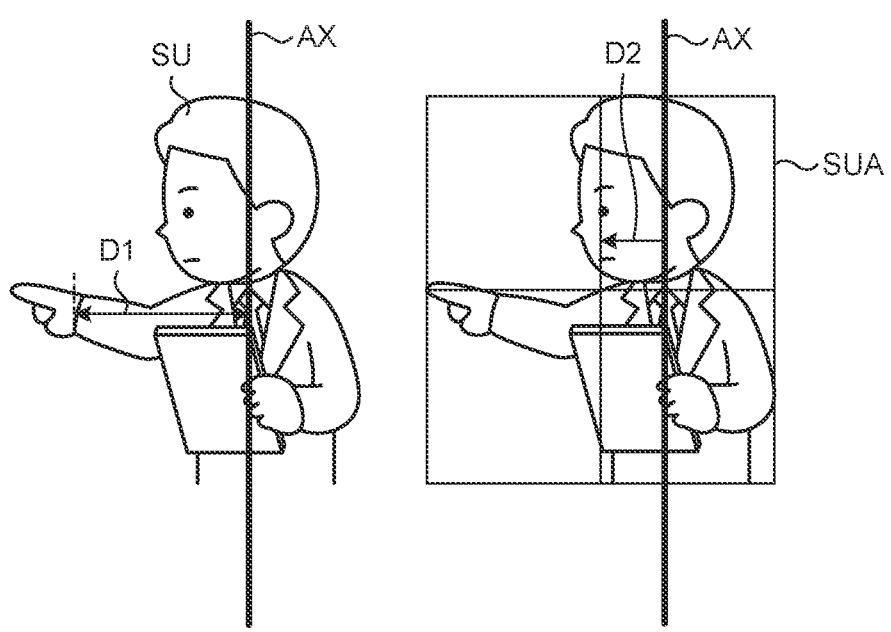
FIG. 6 is a view for describing the method of determining an orientation of a subject.

FIGS. 5 and 6 are views for describing a method of determining the orientation of the subject SU.

The orientation determination unit 13 determines the orientation of the subject SU by using the posture information obtained by the posture acquisition unit 11. The orientation determination is performed based on, for example, a deviation of the body part BP with respect to a body axis AX of the subject SU. For example, in the example of FIG. 5, in a case where a deviation of a position of a nose NS with respect to the body axis AX (a distance d from the body axis AX to the nose NS calculated with a left direction as a positive direction) exceeds a threshold, it is determined that the nose NS faces the left. For the determination, it is also possible to use a deviation of another face part such as an eye EY with respect to the body axis AX. In order to more stably perform the determination, relative positions of a plurality of face parts with respect to the body axis AX can be used at the same time. Since a shoulder width SW in the image narrows when the entire body faces sideways, the robustness of the orientation determination can be enhanced by an index such as whether or not the shoulder width SW is equal to or smaller than a threshold.

In parallel with the above determination, the orientation determination unit 13 determines the orientation of the subject SU based on a pose of the subject SU. For example, a well-balanced video may be obtained by shifting the subject SU from the center of the screen depending on the pose of the subject SU even when the subject SU faces the front. FIG. 6 illustrates an example in which the subject SU gives explanation by spreading the right hand, but in this example, the subject SU is desirably shifted to the right side of the screen. The orientation determination unit 13 detects an orientation bias based on the pose of the subject SU and determines the orientation bias as the orientation of the subject SU.

In the determination based on the pose, for example, information such as whether or not a distance D1 between the right wrist (the fourth joint on the left side of FIG. 4) of the subject SU and the body axis AX exceeds a threshold (the left side of FIG. 6) and whether or not a distance D2 between the center of a subject area SUA and the body axis AX exceeds a threshold (the right side of FIG. 6) can be used. The subject area SUA means an area of the subject SU including a main part of the subject SU to be imaged. For example, in a bust shot, a rectangular area including the joints of the upper body of the subject SU is the subject area SUA. The orientation determination unit 13 determines the orientation by using a plurality of calculation means such as the body axis AX and the face part, and the body axis AX and the pose.

Figure 7:
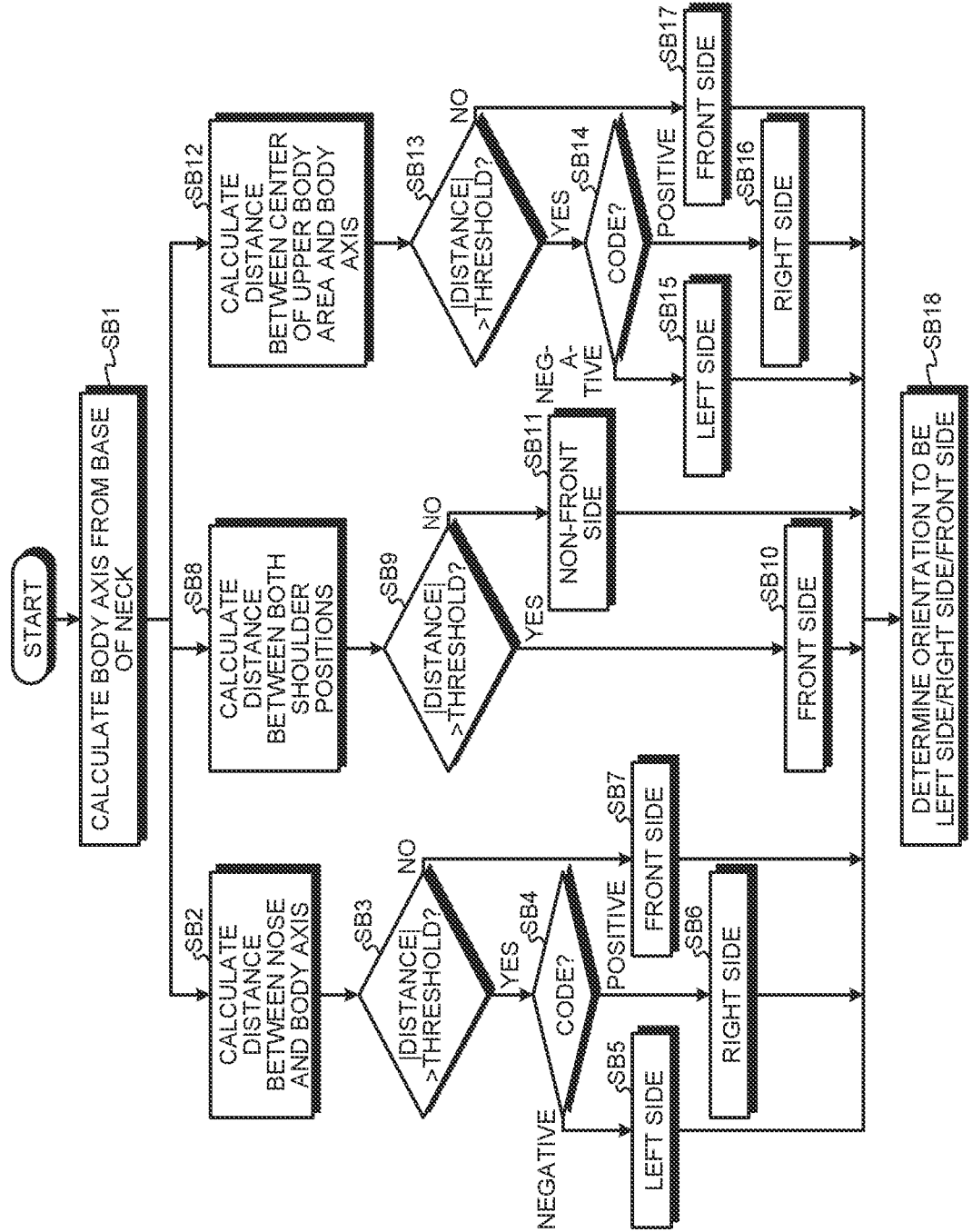
FIG. 7 is a diagram illustrating an example of an orientation determination flow.

FIG. 7 is a diagram illustrating an example of an orientation determination flow.

In FIG. 7, the orientation of the subject SU is determined from a relationship between the nose NS and the body axis AX, the shoulder width SW, and a relationship between the subject area SUA and the body axis AX. The orientation determination unit 13 first calculates the body axis AX along the body from the base of the neck (step SB1). Since the posture of the subject SU assumed in the lecture capture is a standing posture, the body axis AX is usually a line extending vertically from the base of the neck. In FIG. 7, three types of orientation determination processing are performed. Orientation determination based on the face (steps SB2 to SB7), orientation determination based on the shoulder width SW (steps SB8 to SB11), and orientation determination using the subject area SUA (steps SB12 to SB17) from the left in the drawing are performed.

In the orientation determination based on the face (steps SB2 to SB7), whether the nose NS is on the left side or the right side of the screen with respect to the body axis AX is calculated. Assuming that the horizontal axis of the screen is an x axis and the vertical axis is a y axis, the body axis is expressed by a linear expression such as $x=a*y+b$. In a case where coordinates of the nose NS are (x0,y0) with respect to the straight line, the orientation determination unit 13 calculates a signed distance $d=(x0-a*y0-b)/\sqrt{(1+a*a)}$ (step SB2). In a case where the distance d is a positive value, it is determined that the nose NS is on the right side of the body axis AX on the screen. In a case where the distance d is a negative value, it is determined that the nose NS is on the left side of the body axis AX.

In a case where the body axis AX is drawn vertically, $x=b$ when $a=0$, and b corresponds to the x coordinate of the neck. At this time, $d=x0-b$. If the nose NS is on the right side of the body axis AX (x0>b), d>0. If the nose NS is on the left side of the body axis AX (x0<b), d<0. The orientation determination unit 13 determines whether or not an absolute value of the distance d is larger than a threshold (step SB3). In a case where the absolute value of the distance d is equal to or smaller than the threshold (step SB3: no), the orientation determination unit 13 determines that the orientation of the subject SU is the front side (step SB7). In a case where the absolute value of the distance d is larger than the threshold (step SB3: yes), the orientation determination unit 13 determines whether the orientation of the subject SU is the right side or the left side based on the sign of the distance d (steps SB4 to SB6).

In the orientation determination based on the shoulder width SW (steps SB8 to SB11), the orientation determination unit 13 calculates a distance between both shoulders as the shoulder width SW (step SB8). The orientation determination unit 13 determines whether or not an absolute value of the shoulder width SW is larger than a threshold (step SB9). In a case where the absolute value of the shoulder width SW is larger than the threshold (step SB9: yes), the orientation determination unit 13 determines that the orientation of the subject SU is the front side (step SB10). In a case where the absolute value of the shoulder width SW is equal to or smaller than the threshold (step SB9: no), the orientation determination unit 13 determines that the orientation of the subject SU is not the front side (step SB11).

In the orientation determination using the subject area SUA (steps SB12 to SB17), for example, the orientation determination unit 13 calculates, as the subject area SUA, an area including an upper body part obtained by the posture acquisition unit 11. The orientation determination unit 13 calculates the distance D1 between the center of the subject area SUA and the body axis AX by a method similar to the method for calculating the distance d (step SB12). The orientation determination unit 13 determines whether or not an absolute value of the distance D1 is larger than a threshold (step SB13). In a case where the absolute value of the distance D1 is equal to or smaller than the threshold (step SB13: no), the orientation determination unit 13 determines that the orientation of the subject SU is the front side (step SB17). In a case where the absolute value of the distance D1 is larger than the threshold (step SB13: yes), the orientation determination unit 13 determines whether the orientation of the subject SU is the right side or the left side based on the sign of the distance D1 (steps SB14 to SB16).

In this manner, the orientation determination unit 13 comprehensively determines the orientation to be the left side/right side/front side when a plurality of (three) orientation determination results are obtained (step SB18). The orientation determination unit 13 considers a case where the position of the neck cannot be acquired, and in a case where two types of orientation determination results among the three types indicate the same orientation, the orientation determination unit 13 adopts the orientation, thereby increasing the robustness of the orientation. In a case where it is determined in step SB11 that the orientation of the subject SU is not the front side, it is treated that the orientation of the subject SU may be either right side or left side.

Figure 8:
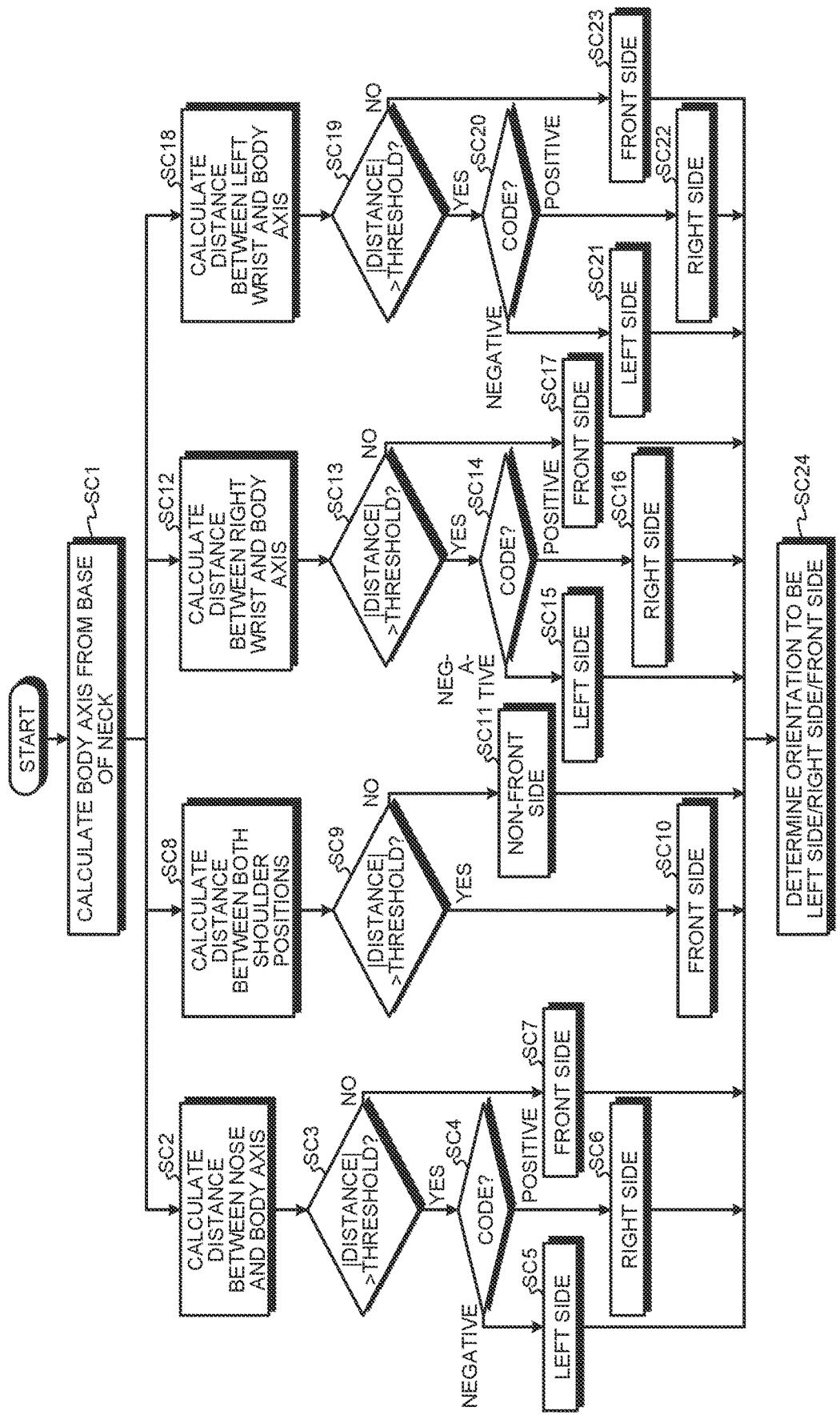
FIG. 8 is a diagram illustrating an example in which orientation determination based on a distance between a wrist and a body axis is performed instead of orientation determination based on a subject area.

FIG. 8 is a diagram illustrating an example in which orientation determination based on the distance D2 between the wrist and the body axis AX is performed instead of the orientation determination based on the subject area SUA. The orientation determination based on the face (steps SC2 to SC7) and the orientation determination based on the shoulder width SW (steps SC8 to SC11) are similar to those in FIG. 7.

The orientation determination unit 13 calculates the distance D2 between the right wrist and the body axis AX by a method similar to the method for calculating the distance d (step SC12). The orientation determination unit 13 determines whether or not an absolute value of the distance D2 is larger than a threshold (step SC13). In a case where the absolute value of the distance D2 is equal to or smaller than the threshold (step SC13: no), the orientation determination unit 13 determines that the orientation of the subject SU is the front side (step SC17). In a case where the absolute value of the distance D2 is larger than the threshold (step SC13: yes), the orientation determination unit 13 determines whether the orientation of the subject SU is the right side or the left side based on the sign of the distance D2 (steps SC14 to SC16).

The orientation determination unit 13 also performs a similar orientation determination flow for the left wrist to that for the right wrist. That is, the orientation determination unit 13 calculates the distance D2 between the left wrist and the body axis AX by a method similar to the method for calculating the distance d (Step SC18). The orientation determination unit 13 determines whether or not the absolute value of the distance D2 is larger than the threshold (step SC19). In a case where the absolute value of the distance D2 is equal to or smaller than the threshold (step SC19: no), the orientation determination unit 13 determines that the orientation of the subject SU is the front side (step SC23). In a case where the absolute value of the distance D2 is larger than the threshold (step SC19: yes), the orientation determination unit 13 determines whether the orientation of the subject SU is the right side or the left side based on the sign of the distance D2 (steps SC20 to SC22).

In the example of FIG. 8, the orientation determination unit 13 determines an overall orientation by using four types of orientation determination results (step SC24). At this time, it is desirable to first integrate the results of determination using the right wrist and the left wrist, and further integrate the integrated determination result with the other two types of determination results. The orientation determination unit 13 determines the orientation of the subject SU based on three types of orientation determination results obtained by combining the integrated one type of determination result and the remaining two types of determination results (the result of the orientation determination based on the face and the result of the orientation determination based on the shoulder width SW).

For example, in a case where both hands are spread, the determination result is divided into the left direction and the right direction based on the right wrist and the left wrist, but it is considered that the body faces the front. Therefore, the orientation determination unit 13 outputs a determination result indicating that the orientation of the subject SU is the front side as the integrated determination result, and performs left/right/front determination based on the integrated determination result and the other two types of determination results. In a case where two types of orientation determination results among the three types indicate the same orientation, the orientation determination unit 13 adopts the orientation. As a result, the robustness of the orientation increases.

As for the threshold used in the flows of FIGS. 7 and 8, an appropriate value is set according to the body part to be measured. The threshold is preferably expressed by a ratio based on a size of a specific part of the subject SU. For example, in a case where the threshold is set to 0.2 times the height of the head area HEA, a change in size of a person due to a zoom variation can be handled.

[1-2-4. Size Determination Unit]

Figure 9:
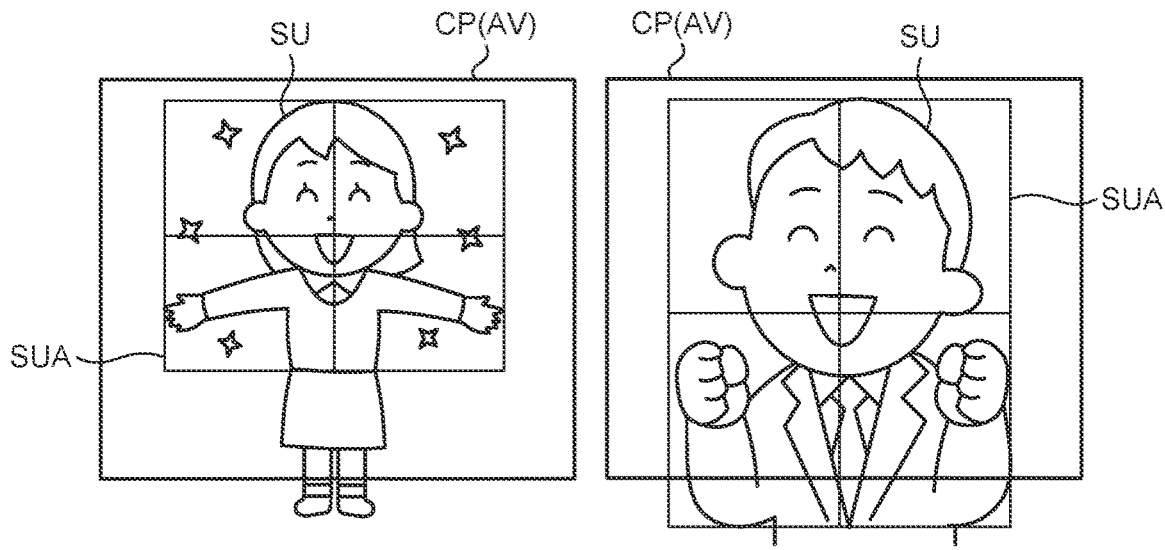
FIG. 9 is a view for describing a method of determining a size of a subject.

FIG. 9 is a view for describing a method of determining the size of the subject SU.

The size determination unit 14 determines whether the pose of the subject SU is large or small. The subject SU expressing joy by spreading both hands HA is illustrated on the left side of FIG. 9. The subject SU doing a small first pump is illustrated on the right side of FIG. 9. For these subjects SU, the size determination unit 14 extracts, for example, an area surrounding the upper body or the entire body of the subject SU as the subject area SUA, and determines the size of the subject area SUA as the size of the subject SU. The size determination result is reflected in the composition CP.

Figure 10:
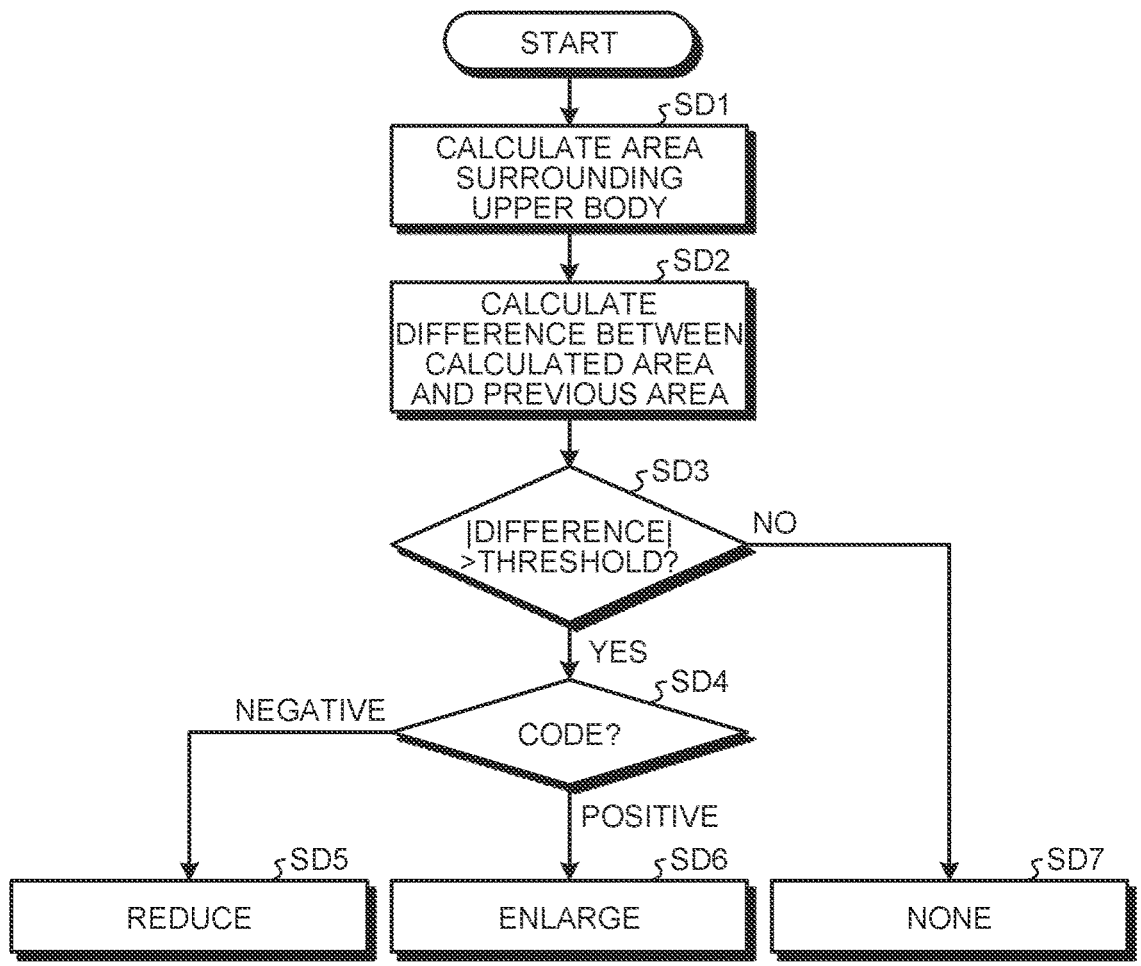
FIG. 10 is a diagram illustrating an example of a size determination flow.

FIG. 10 is a diagram illustrating an example of a size determination flow.

The approximate size of the subject SU is often designated in advance by a user. Here, a description will be made assuming that clipping of a bust shot is designated by the user.

For example, the size determination unit 14 calculates a rectangular area surrounding the upper body of the subject SU as the subject area SUA by using the position of the body part BP and the head area HEA obtained by the posture acquisition unit 11 (step SD1). The size determination unit 14 calculates how large the subject area SUA has become from the previous frame as a difference from the previous frame (step SD2). As the difference, differences in the vertical direction and the horizontal orientation of the subject SU are obtained, and the size determination unit 14 selects, for example, a difference having a larger absolute value.

The size determination unit 14 determines whether or not the absolute value of the calculated difference is larger than a threshold (step SD3). In a case where the absolute value of the difference is equal to or smaller than the threshold (step SD3: no), the size determination unit 14 determines that there is no change in size (step SD7). In a case where the absolute value of the difference is larger than the threshold (step SD3: yes), the size determination unit 14 determines whether the size has been decreased or increased based on a sign of the difference (steps SD4 to SD6).

In a case where the size changes, the size determination unit 14 basically determines a rate of increase and a rate of decrease in angle AV of view (the video area in the captured video CV to be clipped) in such a way as to include the subject area SUA, but the rate of decrease and the rate of increase can also be determined in advance. While it ultimately depends on a user's preference, in a case where the rate of increase and the rate of decrease are determined in advance, the switching of the size of the angle AV of view becomes clear, and an easy-on-the-eye video is obtained.

[1-2-5. Movement Determination Unit]

The movement determination unit 15 calculates the direction and the amount of movement of the subject SU in the current frame with respect to the previous frame based on the subject tracking result obtained by the subject tracking unit 12. The movement determination unit 15 determines whether or not the subject SU has moved based on a result of calculating the movement method and the movement amount.

Figure 11:
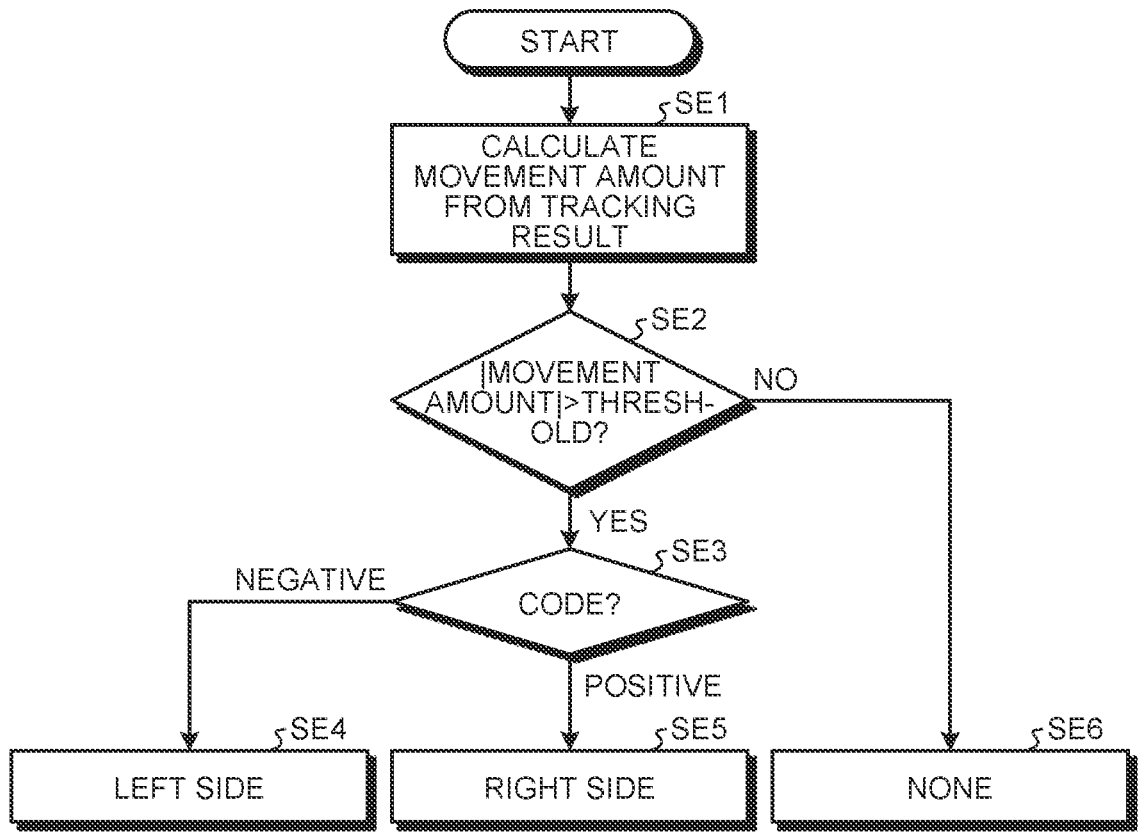
FIG. 11 is a diagram illustrating an example of a movement determination flow.

FIG. 11 is a diagram illustrating an example of a movement determination flow.

The movement determination unit 15 acquires a subject position in the current frame and a subject position in the previous frame based on the tracking result. The subject position is acquired, for example, as coordinates of the subject SU in a camera coordinate system. The movement determination unit 15 calculates the movement amount of the subject SU by subtracting the subject position of the previous frame from the subject position of the current frame (step SE1). For example, the movement amount is calculated as a signed movement amount with the right direction as the positive direction. The movement amount is a positive movement amount when moving to the right side of the screen, and is a negative movement amount when moving to the left side.

The movement determination unit 15 determines whether or not an absolute value of the movement amount is larger than a threshold (step SE2). In a case where the absolute value of the movement amount is equal to or smaller than the threshold (step SE2: no), the movement determination unit 15 determines that the subject SU is not moving (step SE6). In a case where the absolute value of the movement amount is larger than the threshold (step SE2: yes), the movement determination unit 15 determines whether the movement direction is the right direction or the left direction based on the sign of the movement amount (steps SE3 to SE5).

[1-2-6. Target Composition Calculation Unit]

Figure 12:
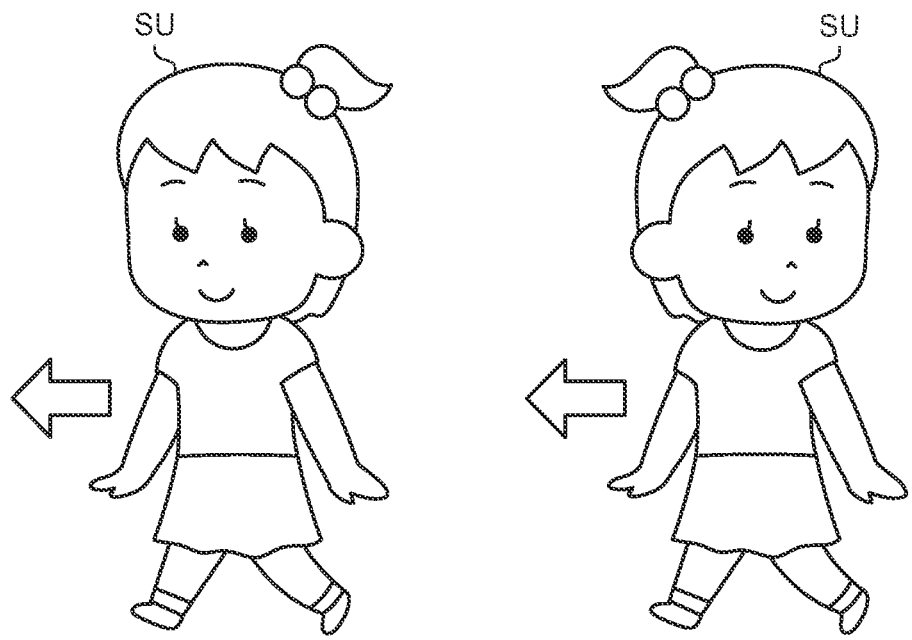
FIG. 12 is a view illustrating a target composition calculation method.

FIG. 12 is a view illustrating a target composition calculation method.

The state of the subject SU is specified by the determination results of the orientation determination unit 13, the size determination unit 14, and the movement determination unit 15. The state of the subject SU includes, for example, a state related to at least one of the movement direction of the subject SU, the orientation of the subject SU, or the size of the subject SU. For example, in the example on the left side of FIG. 12, a state in which the subject SU faces the left and moves in the left direction is detected.

The target composition calculation unit 16 calculates the composition (target composition TCP) of the framing video OV as a target based on the state of the subject SU. For example, the target composition calculation unit 16 determines the size of the target composition TCP (the size of the angle AV of view) based on the size determination result. The target composition calculation unit 16 determines spatial margins on the left and right sides of the subject SU based on the orientation determination result and the movement determination result. As a result, the target composition TCP including the margins on the left and right sides is determined.

As in the example on the right side of FIG. 12, in a case where the subject SU walks while looking back, the movement direction determination result and the orientation determination result for the subject SU may be different. In this case, the movement direction determination result is prioritized. In many cases, the composition CP of the previous frame is continued.

Figure 13:
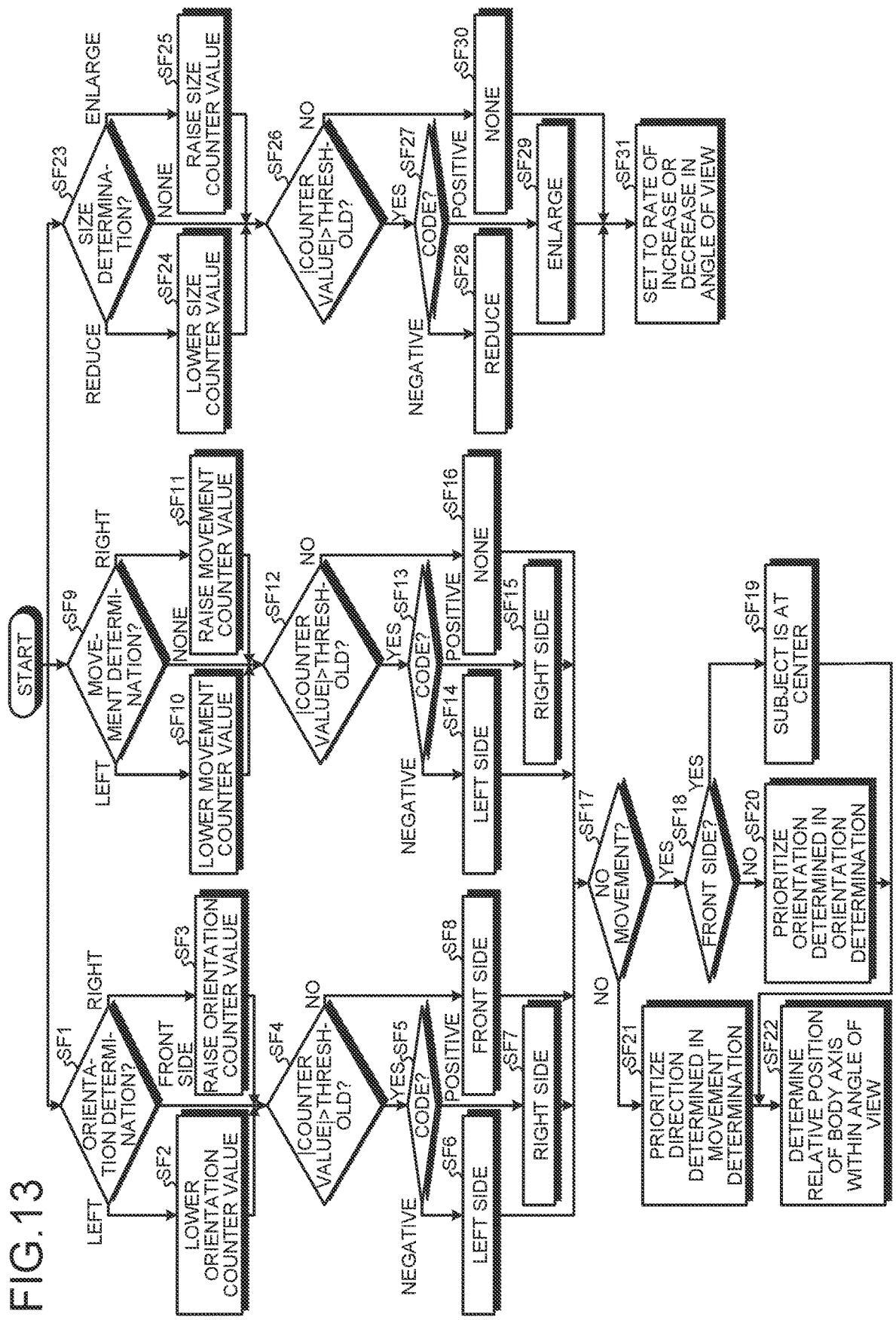
FIG. 13 is a diagram illustrating an example of a target composition calculation flow.
Figure 14:
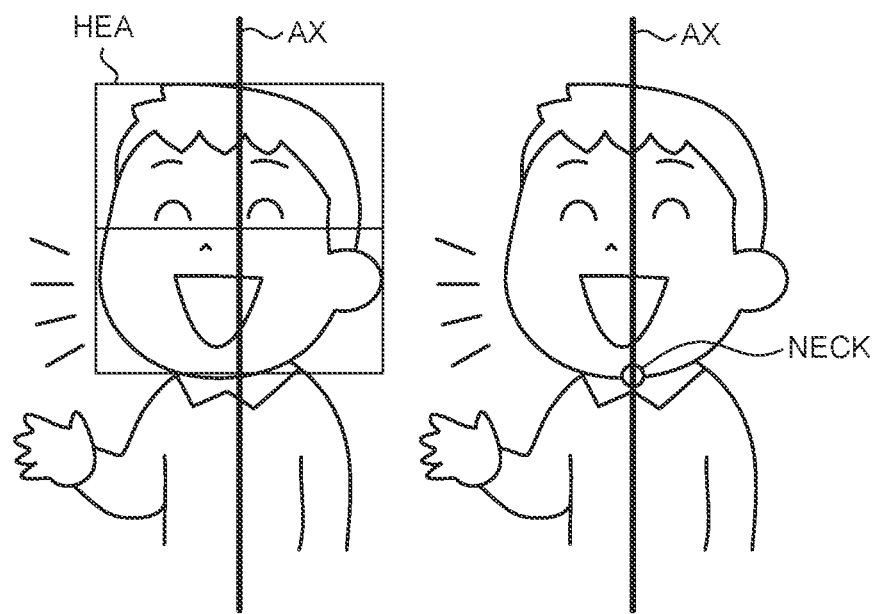
FIG. 14 is a view illustrating the example of the target composition calculation flow.

FIGS. 13 and 14 are views illustrating an example of a target composition calculation flow.

In the flowchart of FIG. 13, stability in the time direction is achieved using an orientation determination counter, a movement determination counter, and a size determination counter cleared in the initial setting (step SA1) of FIG. 3.

The target composition calculation unit 16 lowers a counter value by a preset number in a case where the orientation determination unit 13 determines that the orientation is the left side, and raises the counter value by the same set number in a case where the orientation determination unit 13 determines that the orientation is the right side. In a case where the orientation determination unit 13 determines that the orientation is the front side, the target composition calculation unit 16 does not change the counter value. In a case where an absolute value of the counter value exceeds a threshold, the target composition calculation unit 16 determines that the orientation is the left side or the right side based on a sign of the counter value.

In a case where the movement determination unit 15 determines that the movement direction is the left direction, the movement direction is the right direction, and there is no movement, the target composition calculation unit 16 performs processing of lowering, raising, or not changing a movement counter value. In a case where an absolute value of the counter value exceeds a threshold, the target composition calculation unit 16 determines that there is movement, and determines that the movement direction is the left direction or the right direction based on the sign of the counter value.

The determination results of the orientation determination and the movement determination are used as indices for shifting the subject SU from the center of the screen to provide a margin in a direction indicated by the determination result. In a case where it is determined in the movement determination that the movement direction is the left direction or the right direction, the target composition calculation unit 16 determines a shift amount of the subject SU by giving priority to the determined movement direction. In a case where it is determined in the movement determination that there is no movement, the target composition calculation unit 16 gives priority to the determination result of the orientation determination. In a case where it is determined in the orientation determination that the orientation is the front side, the target composition calculation unit 16 arranges the subject SU at the center of the screen, and in a case where it is determined in the orientation determination that the orientation is the left side or the right side, the target composition calculation unit 16 determines the shift amount of the subject SU in such a way as to provide a margin in the determined direction.

In a case where the size determination unit 14 determines that the subject area SUA is enlarged, the target composition calculation unit 16 raises a size counter value. In a case where the size determination unit 14 determines that the subject area SUA is reduced, the target composition calculation unit 16 lowers the size counter value. As for the size counter, the target composition calculation unit 16 does not change the size of the angle AV of view in a case where the absolute value is equal to or less than a threshold, and determines the increase and decrease of the angle AV of view based on the sign of the size counter value in a case where the absolute value is exceeded.

The output of the target composition calculation unit 16 is, for example, the size of the angle AV of view and the relative position of the body axis AV with the top of the head of the subject SU in the angle AV of view as a start point. For example, the start point is obtained as an intersection of an upper side of the head area HEA and the body axis AX in FIG. 14.

[1-2-7. Composition Transition Determination Unit]

FIGS. 15 to 18 are views for describing a method of transitioning the composition CP. A current composition CCP, the target composition TCP, and the next composition NCP are illustrated as video areas (angle AV of view) to be clipped. The current composition CCP means the composition CP of the video area clipped as the framing video OV of the current frame. The next composition NCP means the composition CP of the video area to be clipped as the framing video OV of the next frame.

The composition transition determination unit 17 determines a transition mode for transition from the current composition CP to the target composition TCP. The composition transition determination unit 17 determines the next composition NCP based on the determined transition mode.

The transition mode includes a smooth composition transition mode and an instantaneous composition transition mode. The smooth composition transition mode is a transition mode in which the composition CP gradually transitions from the current composition CCP to the target composition TCP. The instantaneous composition transition mode is a transition mode in which the composition CP instantaneously transitions from the current composition CCP to the target composition TCP. In the instantaneous composition transition mode, The composition CP transitions quickly in a period shorter than that in the smooth composition transition mode. The term "instantaneous" means, for example, a period within several frames set in advance. The period of the transition is, for example, five frames or less, and preferably one frame.

The composition transition determination unit 17 switches the transition mode for transition to the target composition TCP between the smooth composition transition mode and the instantaneous composition transition mode based on a situation of a change in state of the subject SU. The situation of the change in state of the subject SU includes, for example, a situation related to at least one of a speed at which the movement direction of the subject SU is switched, a speed at which the orientation of the subject SU is switched, and a change in size of the subject SU.

A situation in which the transition mode is to be switched from the smooth composition transition mode to the instantaneous composition transition mode means, for example, a situation in which the type of the target composition TCP changes while the composition smoothly transitions to the target composition TCP.

For example, in a case where the orientation of the subject SU changes from the left side to the right side or from the right side to the left side before the transition to the target composition TCP is completed, a position where the read room is to be provided changes from the left side to the right side or from the right side to the left side. Therefore, another type of target composition TCP in which a direction in which the lead room is provided is different is determined. The type of the target composition TCP also changes in a case where it has become appropriate to change imaging in a bust shot to imaging in a full shot due to a change in pose of the subject SU. In such a case, the transition mode is switched from the smooth composition transition mode to the instantaneous composition transition mode.

The occurrence of the situation in which the transition mode is to be switched from the smooth composition transition mode to the instantaneous composition transition mode means a case where there is a change in orientation or movement direction of the subject SU within a predetermined reference time in which a change in type of the composition may occur as described above, or a case where there is a change in size of the subject SU at a predetermined reference magnification or more. The reference time and the reference magnification can be appropriately set according to the user.

Figure 15:
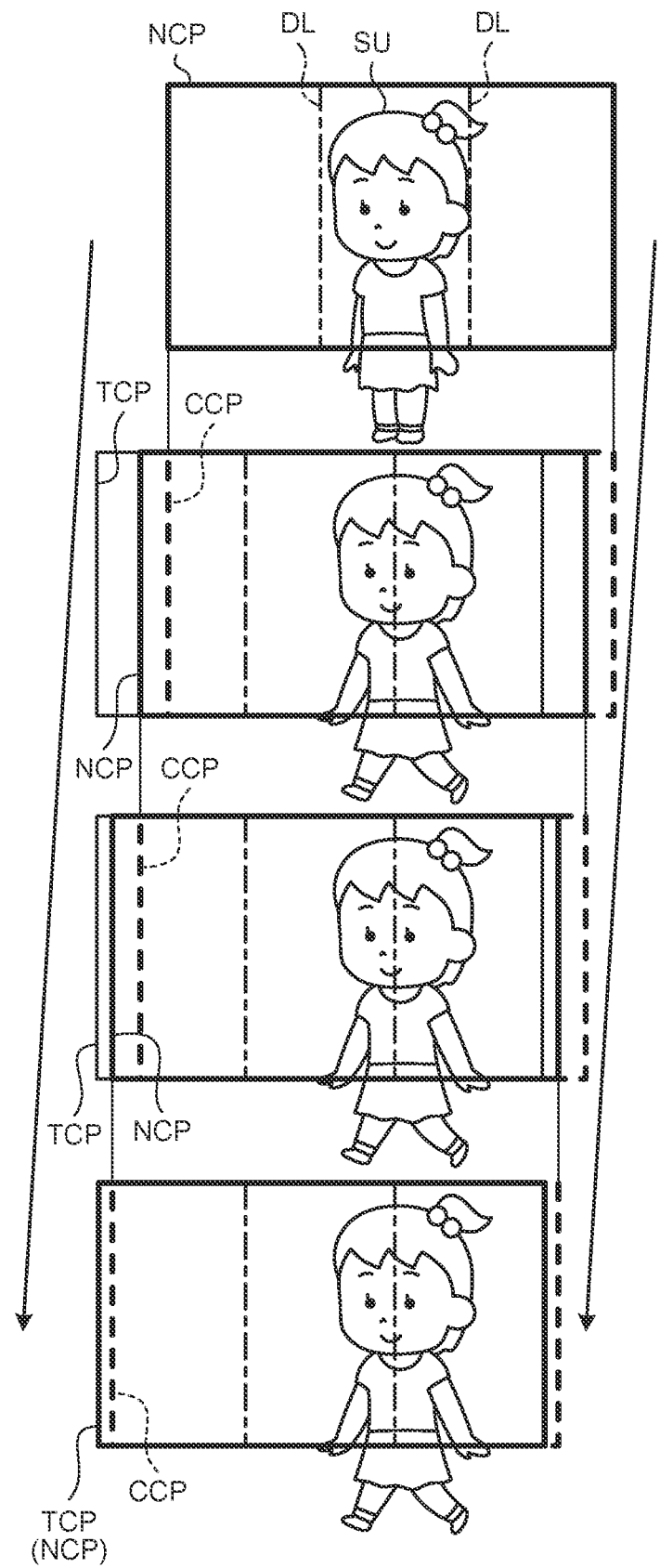
FIG. 15 is a view illustrating smooth composition transition in a case where the subject starts walking from a stationary state.

FIG. 15 is a view illustrating smooth transition of the composition CP in a case where the subject starts walking from a stationary state. In the example of FIG. 15, the target composition TCP is determined based on the rule of thirds. Lines with alternating long and short dashes in FIG. 15 indicate the positions of the division lines DL that divide the screen into three.

In the initial stationary state, the subject SU is arranged at the center of the angle AV of view. When the movement determination unit 15 determines that the subject SU has moved, the target composition calculation unit 16 calculates the position and size of the angle AV of view (a target angle of view) of the target composition TCP in such a way that a margin is provided in a traveling direction. In order to smoothly transition the angle AV of view, the composition transition determination unit 17 calculates a result of interpolation between the angle AV of view of the current composition CCP and the target angle of view as the angle AV of view of the next composition NCP.

The composition transition determination unit 17 generates information regarding the position and size of the angle AV of view of the next composition NCP as the angle-of-view information, and supplies the information to the video clipping unit 18. The composition transition determination unit 17 obtains the angle AV of view of the next composition NCP by interpolation processing, thereby gradually bringing the position and size of the angle AV of view closer to the target angle of view. The smooth transition of the angle AV of view is natural, and is an effective transition method in a case where the movement direction and the orientation of the subject SU do not change frequently.

Figure 16:
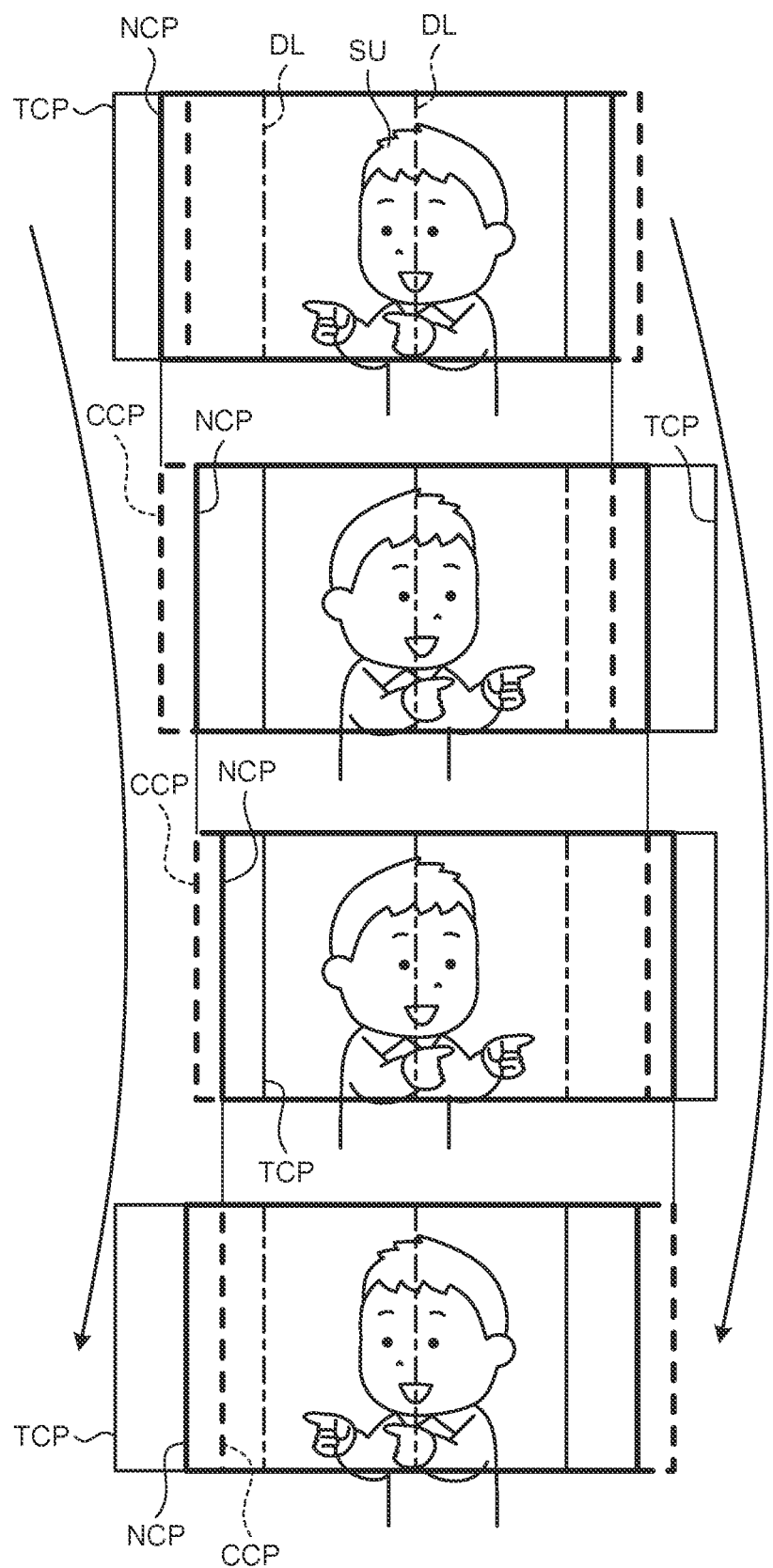
FIG. 16 is a view illustrating an example in which the subject frequently changes the orientation by taking a question, calling, or the like from a student.

FIG. 16 is a view illustrating an example in which the subject SU frequently changes the orientation by taking a question, calling, or the like from a student.

In the example of FIG. 16, even if an attempt is made to gradually transition the angle AV of view to the target angle of view, the orientation of the subject SU changes before the transition is completed. Therefore, the angle of view is not brought close to the target angle of view. In a case where this situation continues, a viewer sees an unsteady change in angle AV of view, which is undesirable. Therefore, the composition transition determination unit 17 instantaneously transitions the composition CP to the target composition TCP.

Figure 17:
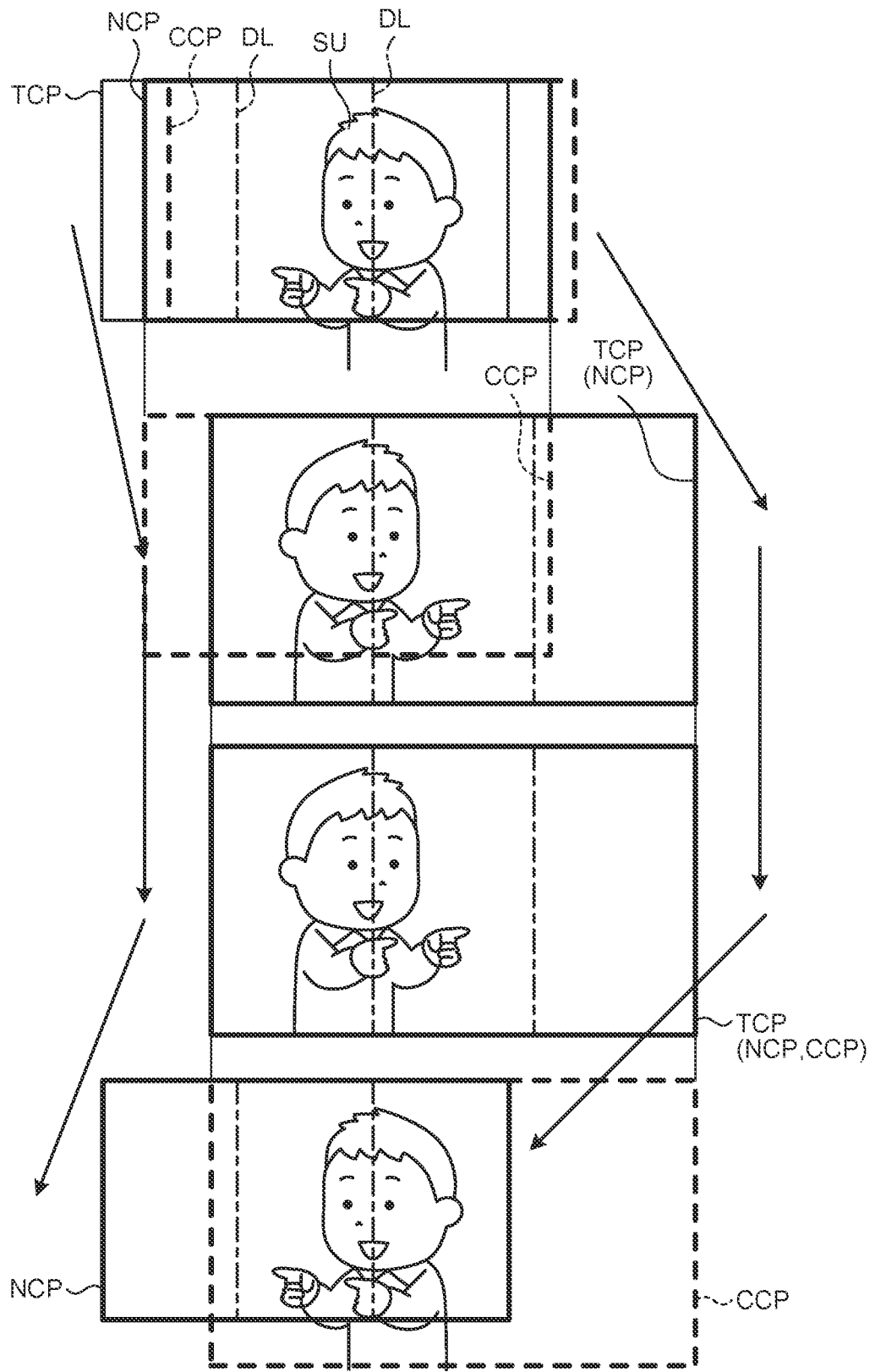
FIG. 17 is a view illustrating an example of composition transition in an instantaneous composition transition mode.

FIG. 17 is a view illustrating an example of transition of the composition CP in the instantaneous composition transition mode.

The composition transition determination unit 17 switches the transition mode to the instantaneous composition transition mode in a case where a new target composition TCP having a different position and size of the target angle of view is determined while the composition CP transitions in the smooth composition transition mode. For example, immediately after the transition is started in the smooth composition transition mode or in a situation in which the composition deviates from the target composition TCP, when the orientation of the subject SU or the like changes and the position and size of the target angle of view are changed, the composition transition determination unit 17 instantaneously transitions the position and size of the angle AV of view of the next composition NCP to the position and size of the target angle of view.

The composition transition determination unit 17 makes a change rate (the rate of increase or the rate of decrease) of the size of the angle AV of view immediately after the transition mode is switched from the smooth composition transition mode to the instantaneous composition transition mode different from a change rate of the size of the angle AV of view immediately before the transition mode is switched. This is because the instantaneous change in composition CP is hardly recognized as a distortion of the video by adjusting the size of the angle AV of view together with the position of the angle AV of view. For example, in a case where only the position of the angle AV of view is changed without changing the change rate of the angle AV of view, an impression as if the camera 20 hits something and the video is distorted may be given. When the size of the angle AV of view is changed, such discomfort is less likely to occur.

Therefore, in a case where the change rate of the size of the angle AV of view at the time of the instantaneous transition calculated from the size of the target angle of view is different from the change rate of the size of the angle AV of view immediately before the instantaneous transition, the composition transition determination unit 17 sets the size of the target angle of view as the size of the angle AV of view of the next composition NCP as it is. When the change rate of the size of the angle AV of view at the time of the instantaneous transition calculated from the target angle of view is the same as the change rate of the size of the angle AV of view immediately before the instantaneous transition, the composition transition determination unit 17 sets an angle of view larger than the target angle of view as the size of the angle AV of view of the next composition NCP.

Although different from the instantaneous transition, it is known that when a video is distributed while switching is performed between a plurality of cameras, a camera switching time is about five seconds to seven seconds at the fastest. This is because switching the camera too quickly gives a viewer a sense of discomfort and does not result in a desirable video. The instantaneous transition of the composition CP is different from the switching of the camera, but when a switching time interval is too short, a desirable video is not obtained similarly to the case of the switching of the camera. Therefore, the composition transition determination unit 17 prohibits selection of the instantaneous composition transition mode for a predetermined period after the instantaneous composition transition mode is selected. In a case where a certain period has not elapsed from the previous instantaneous transition, the composition transition determination unit 17 selects the smooth transition instead of the instantaneous transition.

Figure 18:
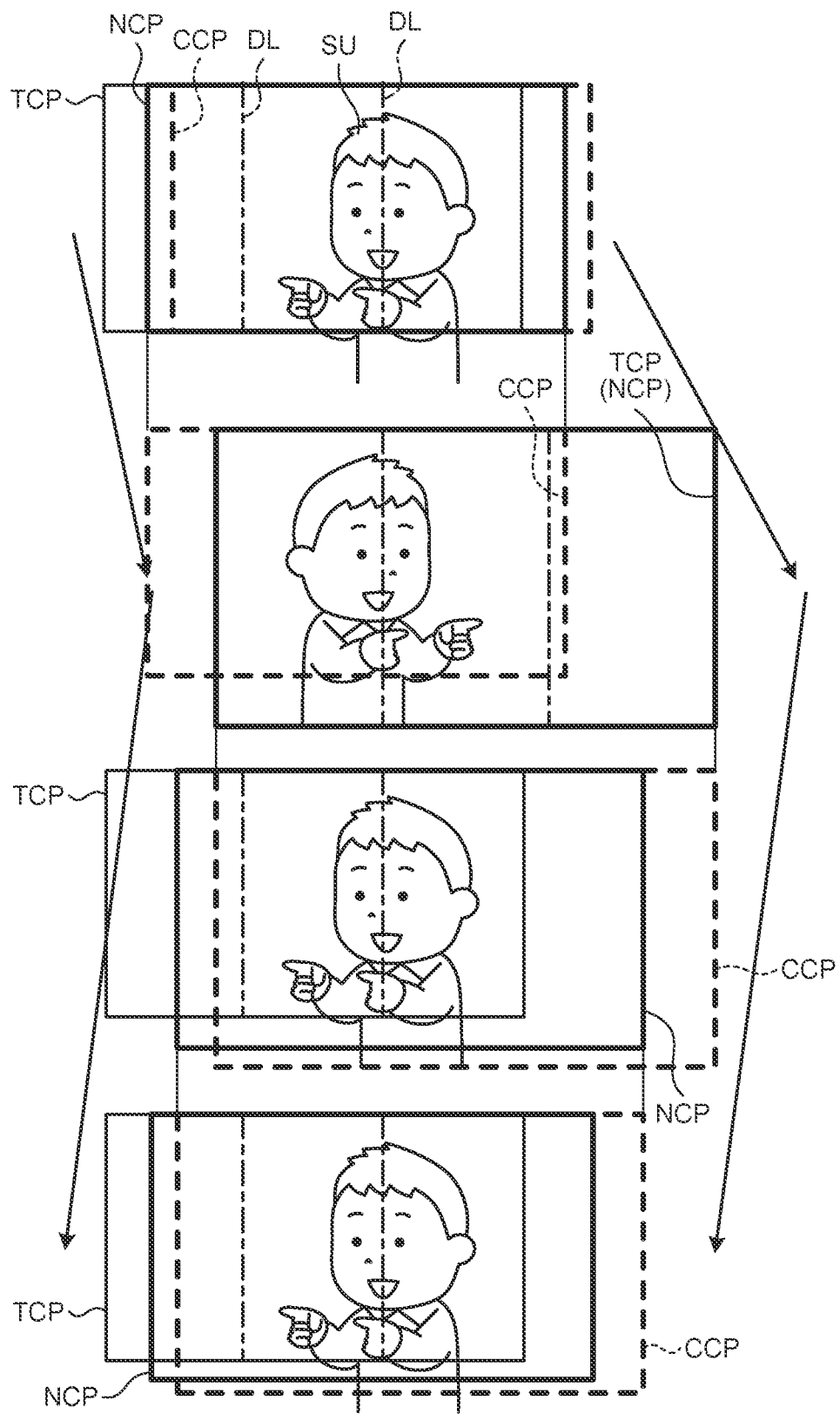
FIG. 18 is a view illustrating an example in which instantaneous transition is first performed and then smooth transition is performed.
Figure 19:
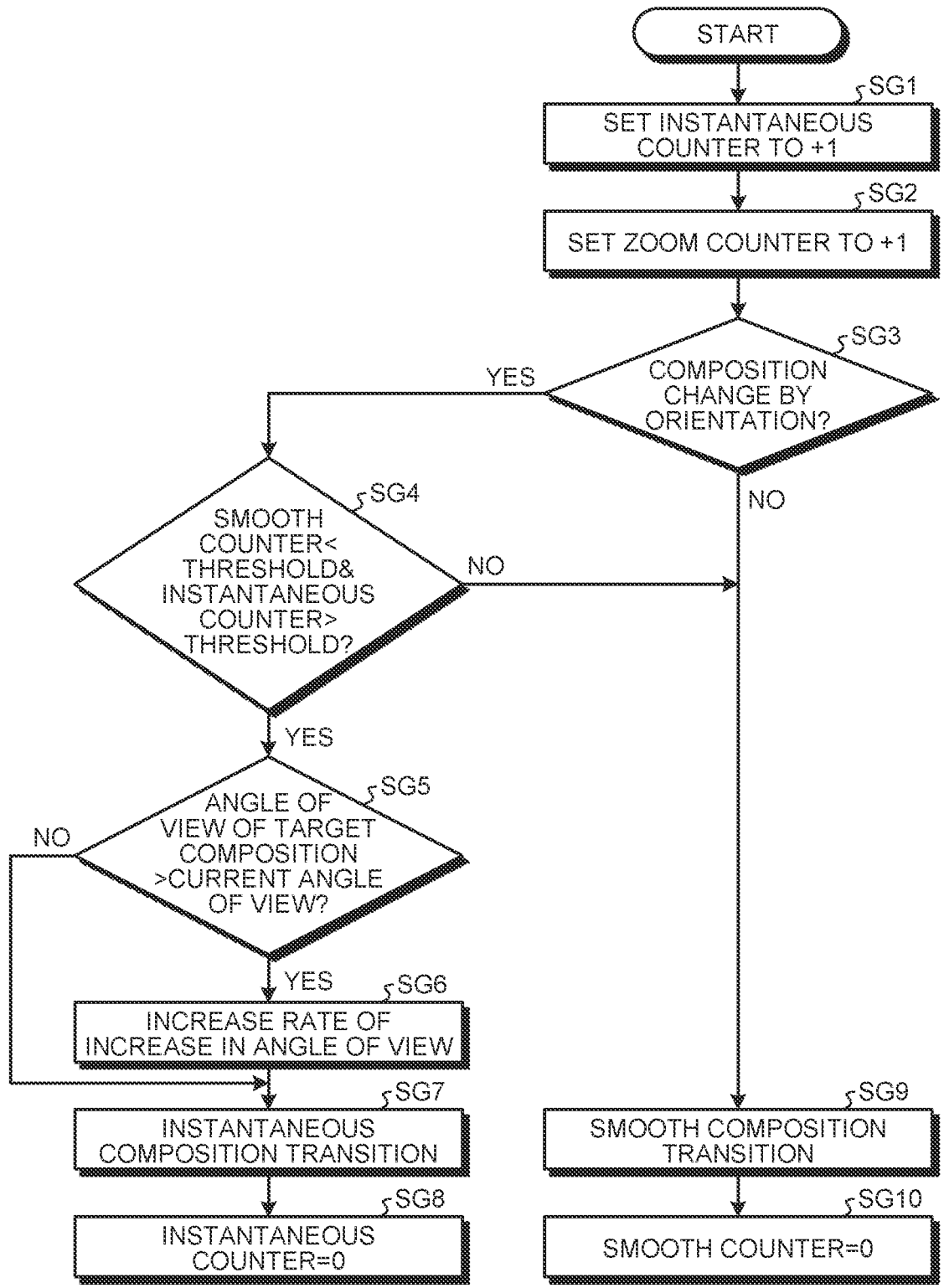
FIG. 19 is a diagram illustrating an example of a transition mode determination flow.

FIG. 18 is a view illustrating an example in which the instantaneous transition is first performed and then the smooth transition is performed. FIG. 19 is a diagram illustrating an example of a transition mode determination flow.

In the flowchart of FIG. 19, the transition of composition CP is performed using an instantaneous counter and a smooth counter cleared in the initial setting (step SA1) of FIG. 3. The instantaneous counter indicates the number of frames after the transition in the instantaneous composition transition mode is performed. The smooth counter indicates the number of frames after the transition in the smooth composition transition mode is performed.

The composition transition determination unit 17 adds 1 to each of the instantaneous counter and the smooth counter for each frame (steps SG1 to SG2). In the instantaneous composition transition mode, the composition transition determination unit 17 clears only the instantaneous counter (step SG8). In the smooth composition transition mode, the composition transition determination unit 17 clears only the smooth counter (step SG10).

In a case where the composition CP calculated by the target composition calculation unit 16 does not change with respect to the composition CP of the previous frame, or in a case where the change does not depend on the change in orientation of the subject SU, the composition transition determination unit 17 selects the smooth composition transition mode (step SG9). Even in a case where the composition CP changes due to the change in orientation of the subject SU, when a value of the smooth counter is equal to or larger than a threshold or a value of the instantaneous counter is equal to or smaller than a threshold, the composition transition determination unit 17 selects the smooth composition transition mode instead of the instantaneous composition transition mode (step SG9).

In a case where the composition CP changes due to the change in orientation of the subject SU, the value of the smooth counter is less than the threshold, and the value of the instantaneous counter exceeds the threshold, the composition transition determination unit 17 selects the instantaneous composition transition mode (step SG7). In a case where the change rate of the angle AV of view of the next frame calculated from the target angle of view (the change rate of the angle AV of view at the time of the instantaneous transition) is the same as the change rate of the angle AV of view of the current frame (the change rate of the angle AV of view immediately before the instantaneous transition), the composition transition determination unit 17 increases the rate of increase in angle AV of view and performs the instantaneous transition of the composition CP.

[1-2-8. Video Clipping Unit]

The video clipping unit 18 clips the video area corresponding to the angle AV of view of the next composition NCP from the captured video CV based on the angle-of-view information acquired from the composition transition determination unit 17. The video clipping unit 18 outputs the clipped video of the video area as the framing video OV.

1-3. Effects

The video processing device 10 includes the target composition calculation unit 16 and the composition transition determination unit 17. The target composition calculation unit 16 calculates the target composition TCP based on the state of the subject SU. The composition transition determination unit 17 switches the transition mode for transition to the target composition TCP between the smooth composition transition mode and the instantaneous composition transition mode based on a situation of a change in state of the subject SU. The smooth composition transition mode is a transition mode in which the composition CP gradually transitions to the target composition TCP. The instantaneous composition transition mode is a transition mode in which the composition CP instantaneously transitions to the target composition TCP. In an information processing method of the present embodiment, processing in the video processing device 10 is performed by a computer. A program of the present embodiment causes a computer to implement processing in the video processing device 10.

With this configuration, an appropriate composition CP corresponding to the change in state of the subject SU can be obtained.

The state of the subject SU includes a state related to at least one of the movement direction of the subject SU, the orientation of the subject SU, or the size of the subject SU. The situation of the change in state of the subject SU includes a situation related to at least one of a speed at which the movement direction is switched, a speed at which the orientation of the subject SU is switched, and a change in size of the subject SU.

With this configuration, an appropriate composition CP corresponding to the situation of the change in movement direction, orientation, and size of the subject SU can be obtained.

The composition transition determination unit 17 makes the change rate of the size of the angle AV of view immediately after the transition mode is switched from the smooth composition transition mode to the instantaneous composition transition mode different from the change rate of the size of the angle AV of view immediately before the transition mode is switched.

With this configuration, the instantaneous change in composition CP is hardly recognized as the distortion of the video.

The composition transition determination unit 17 switches the transition mode to the instantaneous composition transition mode in a case where a new target composition TCP is determined while the composition CP transitions in the smooth composition transition mode.

With this configuration, the shaking of the video due to a frequent change in composition CP is reduced.

The composition transition determination unit 17 prohibits selection of the instantaneous composition transition mode for a predetermined period after the instantaneous composition transition mode is selected.

With this configuration, the discomfort caused by the frequent instantaneous transition of the composition CP is reduced.

The state of the subject SU is acquired by performing image analysis on the captured video CV of the subject SU.

With this configuration, the state of the subject SU can be easily acquired without using a sensor other than the camera.

Note that the effects described in the present specification are merely examples. The effects of the present disclosure are not limited thereto, and other effects may be obtained.

2. Second Embodiment

FIG. 20 is a diagram illustrating an imaging system CS2 according to a second embodiment.

The present embodiment is different from the first embodiment in that a state of a subject SU is acquired based on sensor position information POI of a position sensor SE attached to the subject SU.

Hereinafter, differences from the first embodiment will be mainly described.

The sensor position information POI includes information regarding a position of a body part BP of the subject SU to which the position sensor SE is attached. A video processing device 50 acquires the sensor position information POI via a sensor signal receiver RC. The video processing device 50 performs calibration with a camera 20 and converts the position of the body part BP into a position in a camera coordinate system.

In the present embodiment, processing in a posture acquisition unit 11 or a subject tracking unit 12 (or both of them) is substituted by arithmetic processing using the sensor position information POI. Therefore, the state of the subject SU is accurately detected without performing complicated image analysis.

3. Third Embodiment

3-1. Configuration of Imaging System

Figure 21:
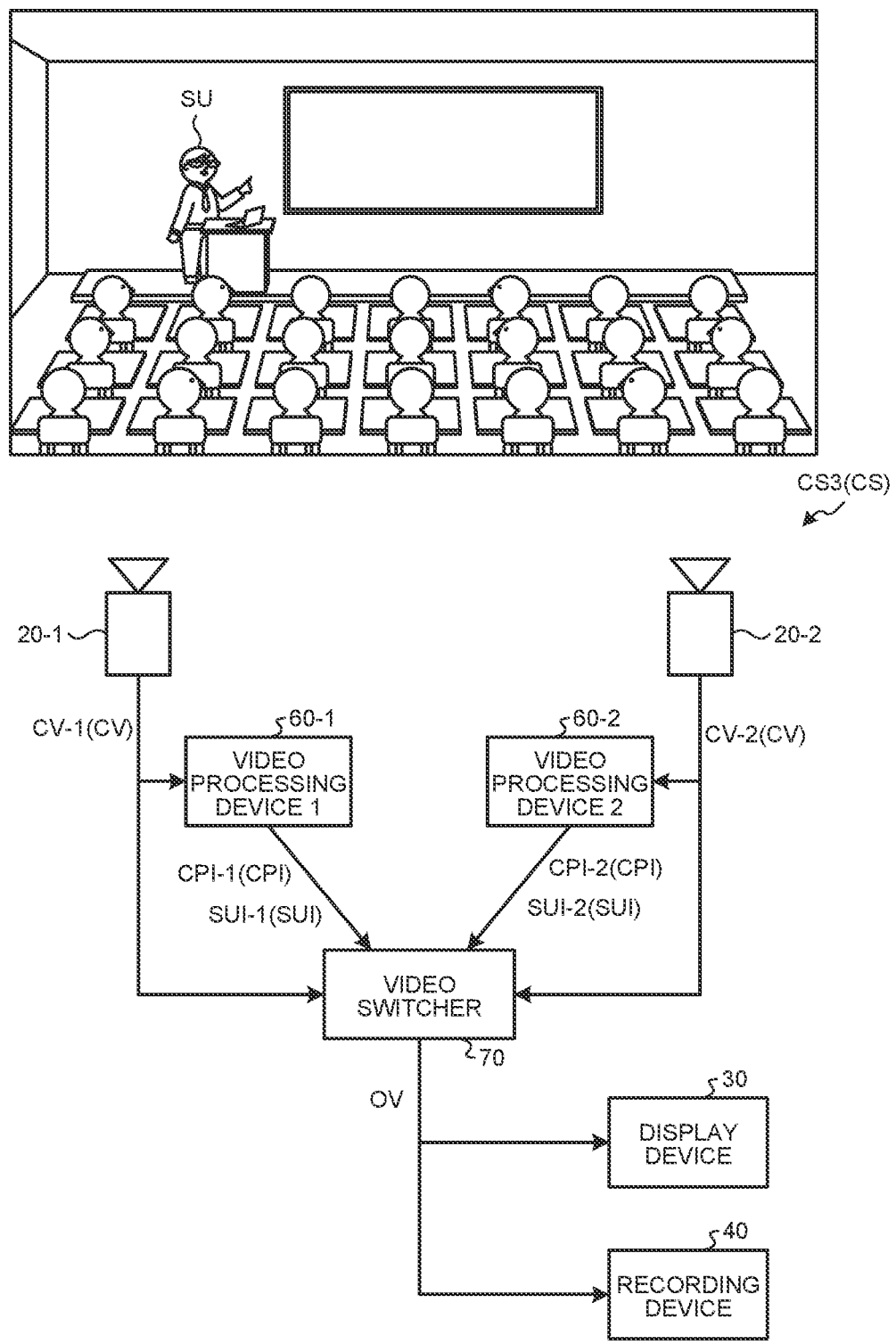
FIG. 21 is a diagram illustrating an imaging system according to a third embodiment.

FIG. 21 is a diagram illustrating an imaging system CS3 according to a third embodiment.

The present embodiment is different from the first embodiment in that a lecture content is recorded using a plurality of cameras 20. Hereinafter, differences from the first embodiment will be mainly described.

A plurality of cameras 20 are installed at an imaging site. The plurality of cameras 20 image a subject SU from different viewpoints. A video processing device 60 is installed for each camera 20. A configuration of the video processing device 60 is similar to that of the video processing device 10 of the first embodiment. In FIG. 21, the individual cameras 20 are distinguished by a number appended after a reference sign. A device and information corresponding to each camera 20 are denoted by the same number as the camera 20 after the reference sign. This number matches, for example, a video number assigned to each captured video CV.

The video processing device 60 performs image analysis on the captured video CV to generate angle-of-view information CPI and subject information SUI. The angle-of-view information CPI indicates a position and size of an angle AV of view (a video area clipped from the captured video CV) corresponding to a composition NCP of the next frame. The subject information SUI indicates a state (a movement direction of the subject SU, an orientation of the subject SU, or a size of the subject SU) of the subject SU. The subject information SUI is generated by a target composition calculation unit 16 based on determination results of an orientation determination unit 13, a size determination unit 14, and a movement determination unit 15.

The imaging system CS3 includes a video switcher 70. The video processing device 60 outputs the angle-of-view information CPI and the subject information SUI to the video switcher 70. The video switcher 70 switches the captured video CV to be subjected to framing based on the subject information SUI acquired from each video processing device 60. The video switcher 70 outputs a framing video OV clipped from the selected captured video CV.

The framing video OV is clipped from the captured video CV based on the angle-of-view information CPI. The clipping of the framing video OV may be performed by the video processing device 60 or may be performed by the video switcher 70. In a case where the video switcher 70 clips the framing video OV, a video clipping unit 18 of the video processing device 60 is not used.

3-2. Configuration of Video Switcher

Figure 22:
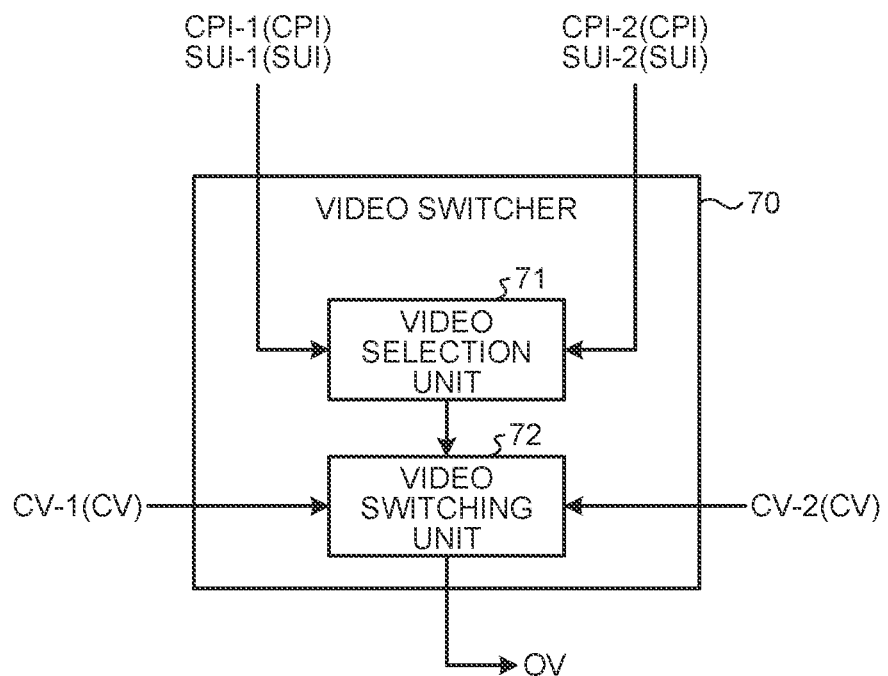
FIG. 22 is a diagram illustrating an example of a functional configuration of a video switcher.

FIG. 22 is a diagram illustrating an example of a functional configuration of the video switcher 70.

The video switcher 70 includes a video selection unit 71 and a video switching unit 72. The video selection unit 71 acquires the subject information SUI and the angle-of-view information CPI from each video processing device 60. The video selection unit 71 selects one captured video CV corresponding to a state of the subject SU from among a plurality of captured videos CV of the subject SU based on a plurality of pieces of acquired subject information SUI.

The video switching unit 72 acquires the angle-of-view information CPI corresponding to the selected captured video CV from the video selection unit 71. The video switching unit 72 clips a video area corresponding to the angle-of-view information CPI from the selected captured video CV. The video switching unit 72 outputs the video area clipped from the selected captured video CV as the framing video OV.

In the video selection unit 71, for example, the captured video CV closer to a front side (or a preset side) is selected using the orientation of the subject SU obtained from the subject information SUI. Alternatively, the captured video CV of the camera 20 close to a direction in which the subject SU approaches is selected using the movement direction of the subject SU obtained from the subject information SUI.

3-3. Video Processing Method

Figure 23:
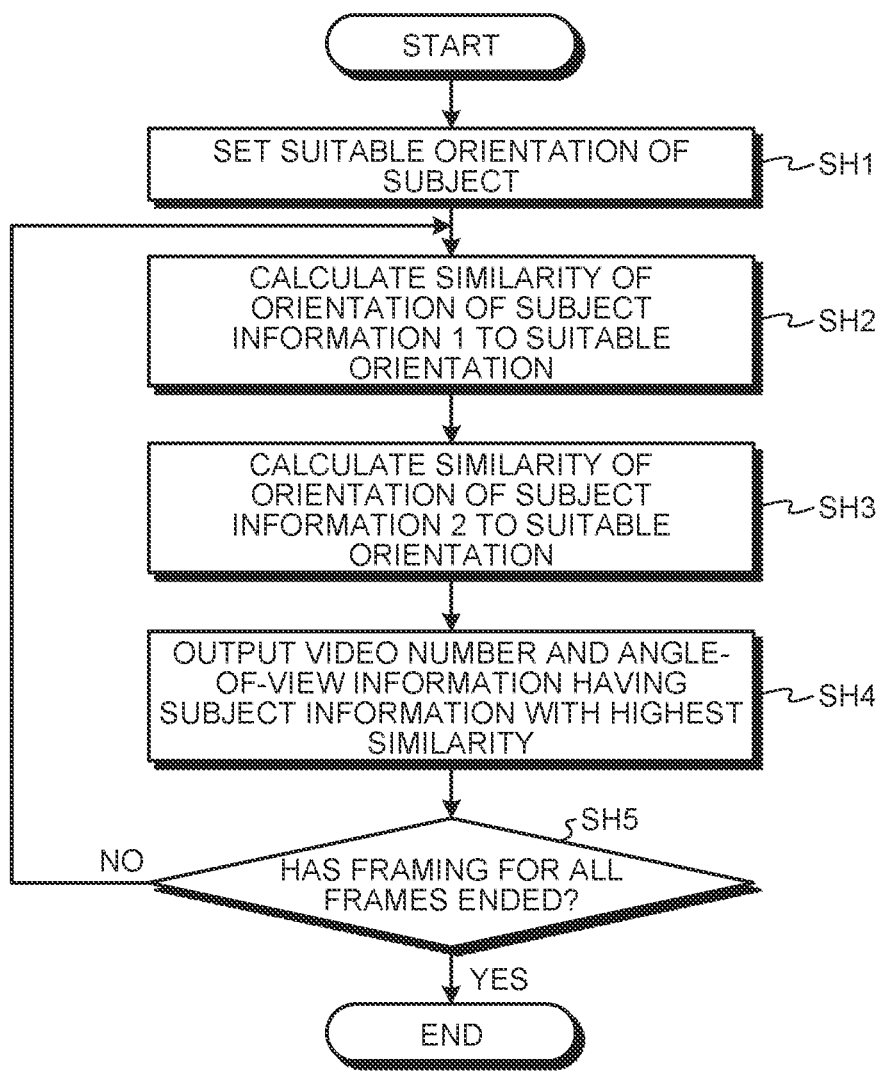
FIG. 23 is a diagram illustrating an example of a captured video selection flow.

FIG. 23 is a diagram illustrating an example of a captured video CV selection flow.

The user sets a suitable orientation of the subject SU (step SH1). By default, for example, the front side is set as the suitable orientation. The video selection unit 71 acquires the subject information SUI and the angle-of-view information CPI synchronized with the captured video CV from the plurality of video processing devices 60. The video selection unit 71 detects the orientation of the subject SU from the subject information SUI for each captured video CV. The video selection unit 71 obtains a similarity between the orientation of the subject SU and the suitable orientation for each captured video CV (steps SH2 and SH3).

The similarity in orientation can be calculated using, for example, a distance d between a nose NS and a body axis AX. Since the distance d is different between a case where the face is directed straight to the side and a case where the face is directed obliquely, the orientation can be more finely set instead of being set to the left side, the right side, and the front side.

The video selection unit 71 detects the captured video CV showing the orientation of the subject SU having the highest similarity. The video selection unit 71 outputs a video number of the detected captured video CV and the angle-of-view information CPI corresponding to the captured video CV to the video switching unit 72 (step SH4). The video switching unit 72 clips the captured video CV indicated by the acquired video number at an appropriate angle AV of view based on the angle-of-view information CPI. The video switching unit 72 outputs the clipped video area as the framing video OV.

The captured video CV (camera 20) is instantaneously switched. In the first embodiment, selection of the instantaneous composition transition mode is prohibited for a predetermined period after the instantaneous composition transition mode is selected. This is to reduce the discomfort caused by the frequent instantaneous transition of the composition CP. For the same reason, it is desirable that the video selection unit 71 prohibit selection of another captured video CV for a predetermined period after one captured video CV is selected. For example, the video selection unit 71 performs the next switching after several seconds from the previous switching. Such control can be performed by providing a counter for measuring a switching interval in the flow of FIG. 23.

At this time, as in the instantaneous composition transition, it is also possible to perform control in such a way as to change the size of the angle AV of view at the time of switching the captured video CV. For example, the video selection unit 71 makes a change rate of the size of the angle AV of view immediately after another captured video CV is selected different from a change rate of the size of the angle AV of view immediately before another captured video CV is selected. Therefore, the instantaneous change in composition CP is hardly recognized as the distortion of the video.

3-4. Effects

In the present embodiment, the video selection unit 71 selects one captured video CV corresponding to the state of the subject SU from among a plurality of captured videos CV of the subject SU captured from different viewpoints. The video switching unit 72 outputs the video area clipped from the selected captured video CV as the framing video OV.

With this configuration, the viewpoint (camera 20) is selected based on the state of the subject SU. The framing video OV is clipped from the captured video CV of the selected viewpoint, whereby a video with a more appropriate composition CP is obtained.

4. Fourth Embodiment

Figure 24:
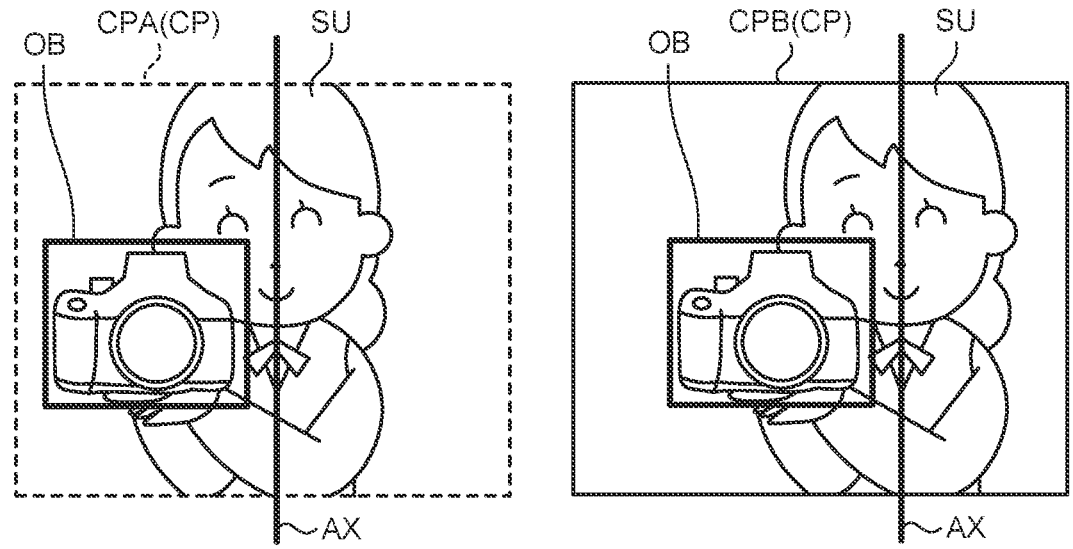
FIG. 24 is a view for describing an outline of framing according to a fourth embodiment.
Figure 25:
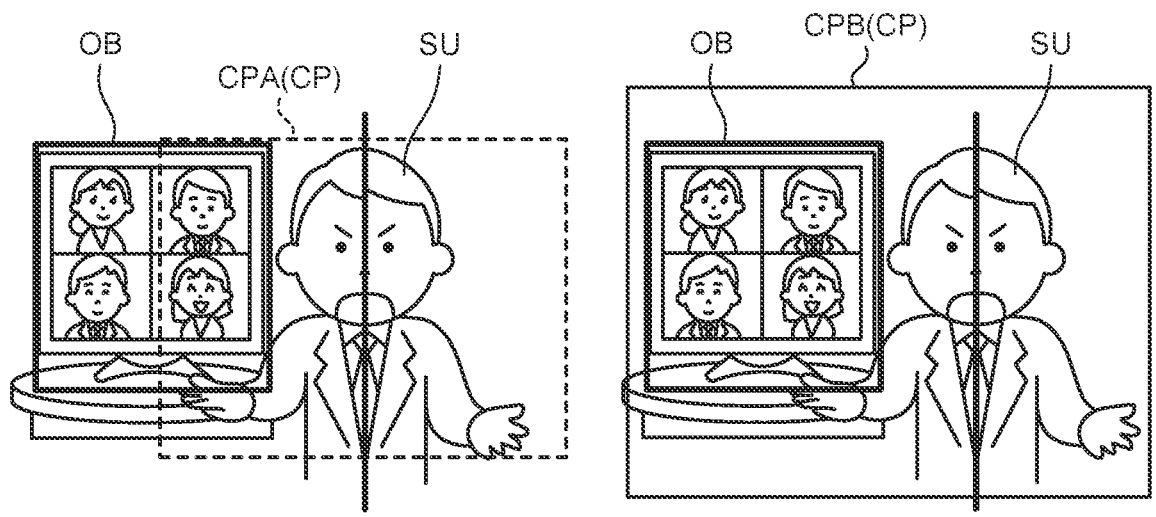
FIG. 25 is a view for describing the outline of framing according to the fourth embodiment.
Figure 26:
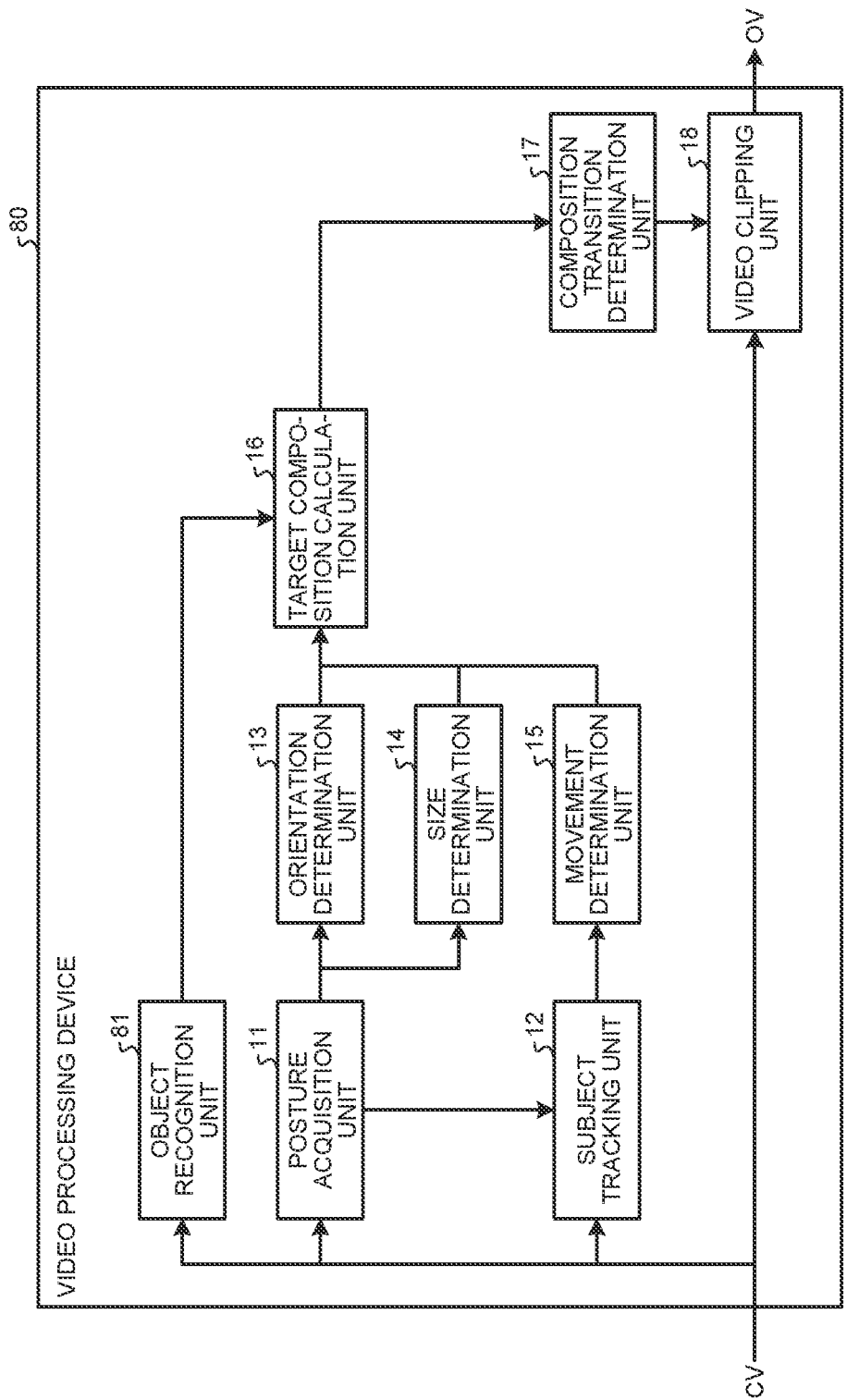
FIG. 26 is a diagram illustrating an example of a functional configuration of a video processing device.

FIGS. 24 and 25 are views for describing an outline of framing according to a fourth embodiment. FIG. 26 is a diagram illustrating an example of a functional configuration of a video processing device 80.

The present embodiment is different from the first embodiment in that a specific object OB is a target of a composition CP together with a subject SU. Hereinafter, differences from the first embodiment will be mainly described.

When a target composition TCP is calculated, not only the subject SU but also the specific object OB may be simultaneously considered. For example, in a scene of advertising a new product as illustrated in FIG. 24, it is desirable to determine a composition CP including not only a speaker (the subject SU) but also a product (the object OB).

In the example on the left side of FIG. 24, only the speaker is a basis of calculation of a composition CPA. An area including only the speaker is extracted as a subject area. The center line of the subject area coincides with a body axis AX, and the body axis AX is arranged at the center of the screen. However, a viewer pays attention not only to the speaker but also to the product. Therefore, there is a possibility that the video is recognized as a leftward-biased video as a whole.

In the example on the right side of FIG. 24, the speaker and the product are bases of calculation of a composition CPB. An area including the speaker and the product is extracted as the subject area, and the center line of the subject area is arranged at the center of the screen. In the composition CPB, since an area of interest to the viewer is arranged at the center of the screen, a well-balanced video can be obtained.

The same applies to a video of a broadcast program incorporating a video conference as illustrated in FIG. 25. In this type of video, it is desirable to determine a composition CP including not only a main speaker (the subject SU) but also a monitor (the object OB) on which video conference participants are displayed.

In the example on the left side of FIG. 25, only the main speaker is the basis of calculation of the composition CPA, and the monitor on the left side is not a target of the composition CP. Therefore, there is a possibility that the video is recognized as a leftward-biased video as a whole. In the example on the right side of FIG. 25, not only the main speaker but also the monitor are the bases of the calculation of the composition CPB, so that a well-balanced video can be obtained.

In order to reflect such a situation, it is preferable to use the video processing device 80 as illustrated in FIG. 26 in which an object recognition unit 81 is added to the video processing device 10 of FIG. 2. The object recognition unit 81 detects the object OB which is the basis of calculation of the target composition TCP together with the subject SU from a captured video CV of the subject SU. With this configuration, the target composition TCP is calculated also based on an object recognition result. Therefore, a video with an appropriate composition CP including the target object OB can be obtained.

5. Fifth Embodiment

5-1. Functional Configuration of Video Processing Device

Figure 27:
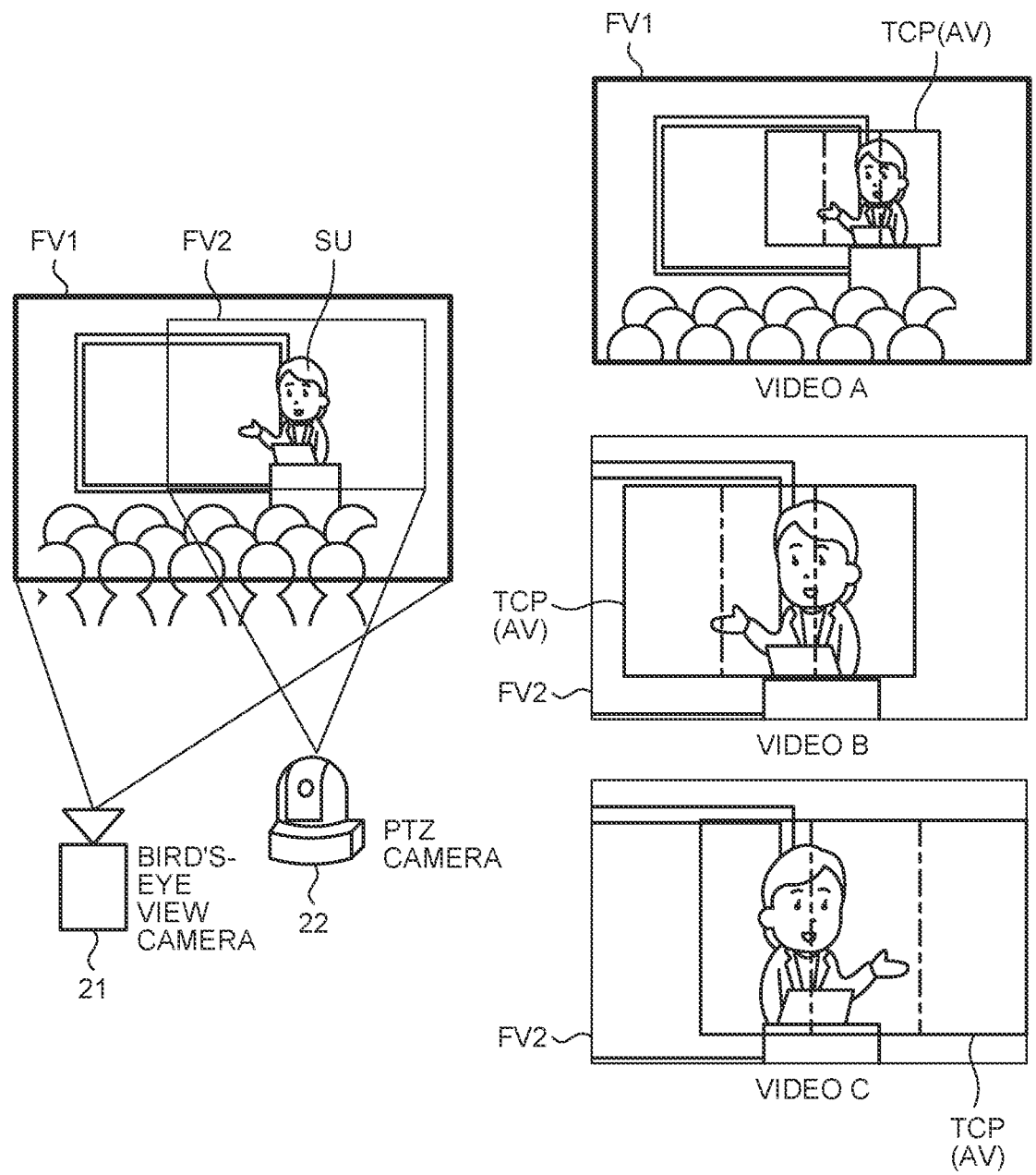
FIG. 27 is a diagram for describing an outline of framing according to a fifth embodiment.
Figure 28:
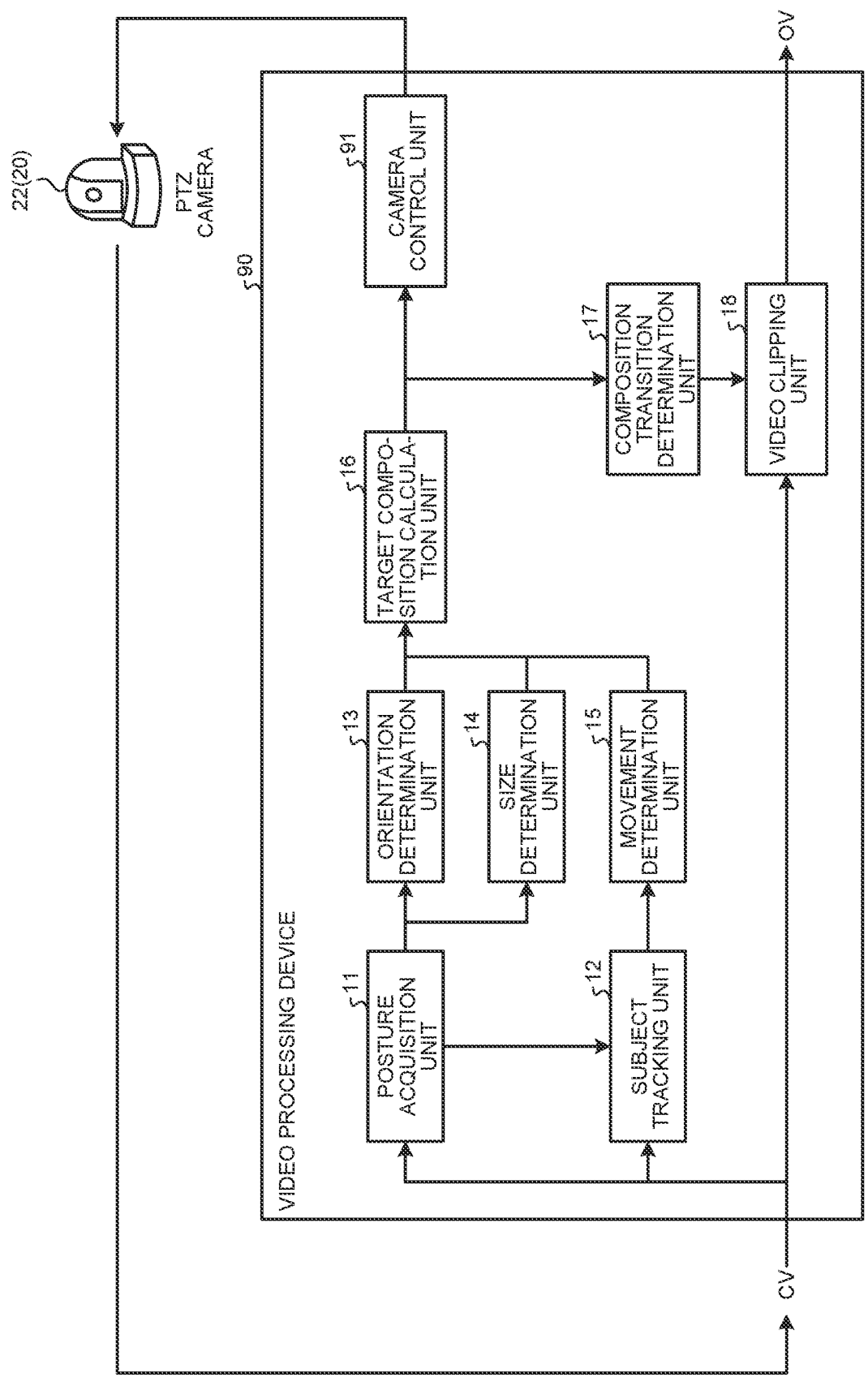
FIG. 28 is a diagram illustrating an example of a functional configuration of a video processing device.

FIG. 27 is a diagram for describing an outline of framing according to a fifth embodiment. FIG. 28 is a diagram illustrating an example of a functional configuration of a video processing device 90.

The present embodiment is different from the first embodiment in that a pan-tilt-zoom (PTZ) camera 22 is used as a camera 20. Hereinafter, differences from the first embodiment will be mainly described.

In the first embodiment, a fixed camera (bird's-eye view camera) having a fixed visual field, in which the entire range in which a subject SU moves around is included in an angle of view, is used as the camera 20. However, the camera 20 is not limited to a fixed camera. For example, similar processing can be performed using the PTZ camera 22. In the PTZ camera 22, since an orientation (pan or tilt) of a lens and zoom can be controlled, a high-quality video can be obtained as compared with the fixed camera.

The left side of FIG. 27 illustrates a difference in visual field between a fixed camera 21 and the PTZ camera 22 when the subject SU is imaged. In a case where the fixed camera 21 is used, a movement range of the subject SU (lecturer) is assumed, and a video of the subject SU who is giving a lecture cannot be output unless a range including the entire movement range is included in a visual field FV1. In this regard, since the lens of the PTZ camera 22 can be turned, it is possible to image the subject SU with high resolution in a narrowed visual field FV2.

A video A on the right side of FIG. 27 is a video captured by the fixed camera 21. A video area (the angle AV of view) near the subject SU is clipped from a wide range of video, and most of the imaging resolution is not used for output.

A video B is a video captured by the PTZ camera 22 in consideration of instantaneous transition. The lens of the PTZ camera 22 is turned by mechanical control, and thus, instantaneous transition of a composition CP cannot be made. Therefore, the visual field FV2 having a margin larger than that of the target composition TCP is imaged in consideration of the video range to be subjected to framing after the instantaneous transition. If the visual field FV2 is set in such a way that a target composition TCP (including an increase in angle AV of view at the time of the instantaneous transition) can be included even in a case of the subject SU whose orientation is opposite to that in the video B as in a video C, the instantaneous transition of the composition CP can be made.

As is clear from the comparison between the video A and the videos B and C, in the present embodiment, framing with higher quality than that of the fixed camera 21 is performed by utilizing the imaging resolution of the PTZ camera 22.

FIG. 28 illustrates a video processing device 90 to which a camera control unit 91 for controlling the PTZ camera 22 is added. The camera control unit 91 controls the visual field (pan, tilt, or zoom) of the PTZ camera 22 that images the subject SU based on the state (a movement direction of the subject SU, an orientation of the subject SU, or a size of the subject SU) of the subject SU.

For example, in a case where the subject SU faces the right side, the camera control unit 91 sets the visual field of the PTZ camera 22 in such a way that a spatial margin is provided on the right side of the subject SU. However, in a case where the subject SU changes the orientation to the left side, when there is no spatial margin on the left side of the subject SU, a video area having an appropriate composition CP for the left-side orientation cannot be clipped. Therefore, the camera control unit 91 sets the visual field of the PTZ camera 22 in such a way that a similar spatial margin is also provided on the left side of the subject SU, so that the composition can instantaneously transition to the composition CP for the left-side orientation. As a result, it is possible to cope with the instantaneous transition of the composition CP while increasing the resolution of a framing video OV.

5-2. Video Processing Method

Figure 29:
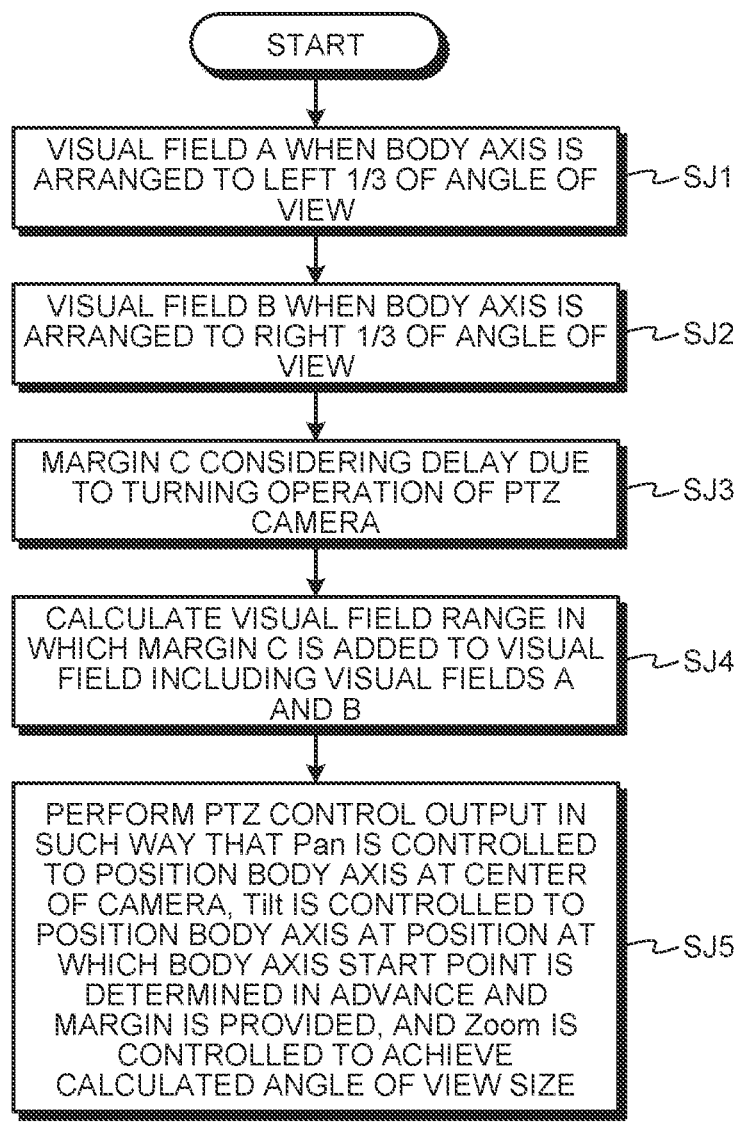
FIG. 29 is a diagram illustrating an example of a control flow of a pan-tilt-zoom (PTZ) camera.

FIG. 29 is a diagram illustrating an example of a control flow of the PTZ camera 22.

The camera control unit 91 outputs a control signal for the PTZ camera 22 based on a position of a body axis AX of the subject SU and an assumed maximum visual field. For example, the camera control unit 91 calculates a visual field in a case where the body axis AX is arranged to the left ⅓ of the screen (step SJ1), and calculates a visual field in a case where the body axis AX is arranged to the right ⅓ of the screen (step SJ2). The camera control unit 91 calculates a margin considering a delay due to a turning operation of the PTZ camera 22 (step SJ3).

The camera control unit 91 calculates a visual field including the two visual fields calculated in steps SJ1 and SJ2, adds the margin calculated in step SJ3 to the visual field, and calculates a range of the visual field to be imaged by the PTZ camera 22 (step SJ4). The camera control unit 91 controls the pan, tilt, and zoom of the PTZ camera in such a way as to obtain the calculated visual field (step SJ5).

For example, the camera control unit 91 sets the pan and tilt in such a way that the body axis AX starting from the top of the head is arranged at the center of the screen, and sets the zoom in such a way that the size of the calculated visual field is obtained. As a result, a video corresponding to the video B in FIG. 27 is acquired.

5-3. Effects

In the present embodiment, the visual field of the PTZ camera 22 is appropriately controlled by the camera control unit 91. Therefore, a high-resolution video having an appropriate composition can be obtained.

6. First Modified Example

In the first embodiment, the transition mode transitions to the instantaneous composition transition mode in a case where a new target composition TCP is determined while the composition CP transitions in the smooth composition transition mode. However, a timing at which the transition mode is switched to the instantaneous composition transition mode is not limited thereto. For example, the composition transition determination unit 17 can switch the transition mode to the instantaneous composition transition mode in a case where the state of the subject SU greatly changes beyond an allowable criterion while the composition CP transitions in the smooth composition transition mode.

The allowable criterion means a criterion related to a state change amount that necessitates a change of the target composition TCP. In a case where the state of the subject SU greatly changes beyond the allowable criterion, it is determined that the target composition TCP cannot be maintained.

For example, in a case where the subject SU widely spreads both hands or starts to talk with a gesture from a stationary state, the size of the subject SU greatly changes. A bust shot may be appropriate in a stationary state, but a waist shot, a knee shot, a full figure, a long shot, or the like may be appropriate in a case where the size of the subject SU greatly changes. In a case where the state of the subject SU greatly changes, and as a result of which the target composition TCP needs to be changed, the composition transition determination unit 17 switches the composition CP in the instantaneous composition transition mode.

With this configuration, discomfort caused by a sense of incompatibility between the state of the subject SU and the composition CP is reduced. When the state of the subject SU greatly changes, it takes time for the change of the composition CP to catch up with the state of the subject SU in a case of the smooth transition of the composition CP. When a time for which the sense of incompatibility occurs between the state of the subject SU and the composition CP becomes long, the viewer feels uncomfortable. In a case where the state of the subject SU greatly changes, if the composition CP instantaneously transitions to the target composition TCP, such discomfort is less likely to occur.

7. Second Modified Example

The framing method of the fifth embodiment can also be applied to a case where imaging is performed with a handheld camera. The handheld camera is common to the PTZ camera 22 in that the visual field can be adjusted by the orientation of the lens. Therefore, similarly to the PTZ camera 22, the camera control unit 91 can control the visual field of the camera 20 that images the subject SU based on the state of the subject SU. For example, the camera control unit 91 performs automatic control of zooming of the handheld camera in such a way that imaging can be performed in a visual field capable of coping with orientation reversal and enlargement and reduction of the composition.

The camera control unit 91 can also notify the user who images the subject of recommendation information based on a difference between a visual field of the current frame and a target visual field. For example, in order to bring the current visual field of the handheld camera closer to the target visual field, the camera control unit 91 presents the recommendation information regarding a change in panning direction, zoom ratio, or the like in a finder. This makes it possible to prompt the user to change the visual field.

8. Third Modified Example

The control method for the PTZ camera 22 described in the fifth embodiment can be combined with the framing method of the third embodiment. At this time, the next angle AV of view is assumed based on the angle AV of view of the currently output framing video OV, and an unselected visual field of the PTZ camera 22 is adjusted to the visual field corresponding to the next angle AV of view. For example, the camera control unit 91 calculates the visual field of the PTZ camera 22 that has captured an unselected captured video CV based on the angle AV of view of the video area clipped from the selected captured video CV. As a result, it is possible to smoothly cope with a change in orientation or movement direction of the subject.

9. Hardware Configuration Example of Imaging System

Figure 30:
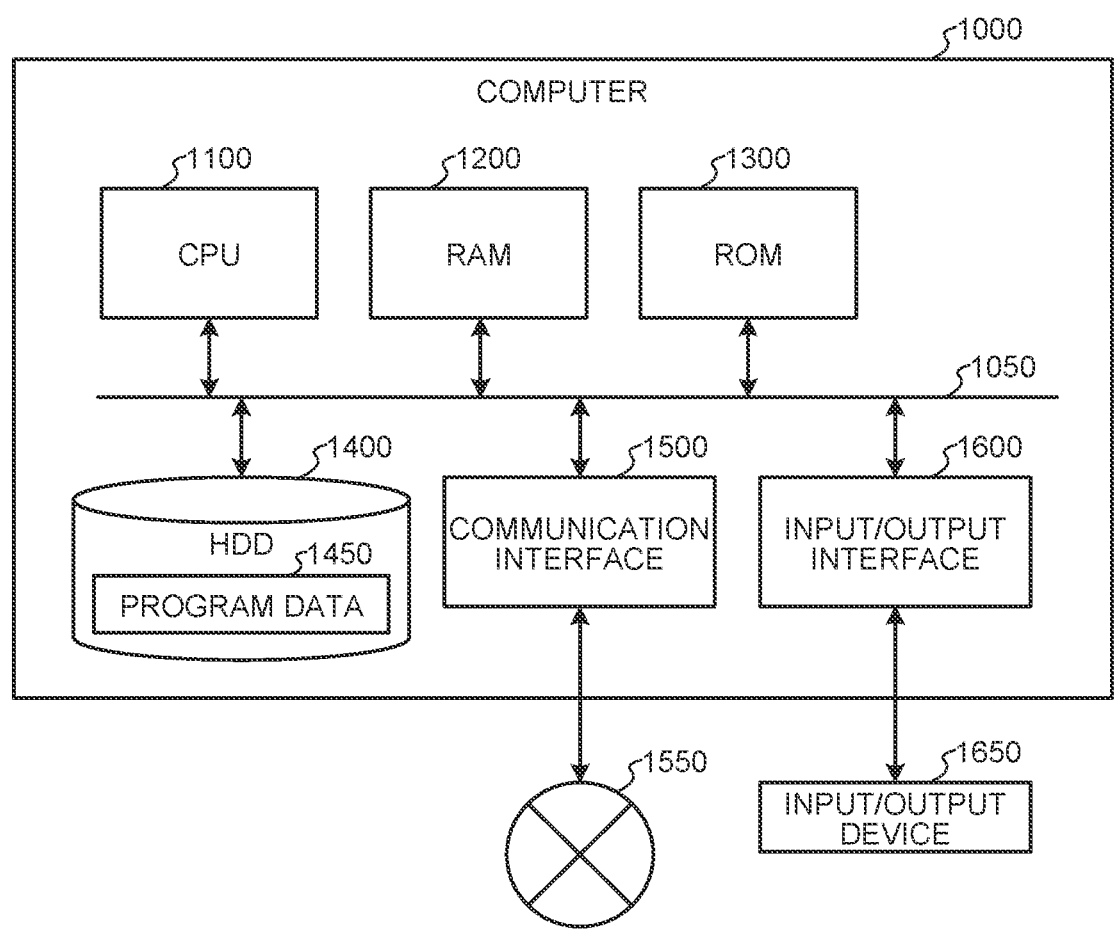
FIG. 30 is a diagram illustrating a hardware configuration example of the imaging system.

FIG. 30 is a diagram illustrating a hardware configuration example of the imaging system CS.

The imaging system CS is implemented by, for example, a computer 1000 having a configuration as illustrated in FIG. 30. The computer 1000 includes a CPU 1100, a RAM 1200, a read only memory (ROM) 1300, a hard disk drive (HDD) 1400, a communication interface 1500, and an input/output interface 1600. Each component of the computer 1000 is connected by a bus 1050.

The CPU 1100 is operated based on a program stored in the ROM 1300 or the HDD 1400, and controls each component. For example, the CPU 1100 loads the program stored in the ROM 1300 or the HDD 1400 on the RAM 1200 and performs processing corresponding to various programs.

The ROM 1300 stores a boot program such as a basic input output system (BIOS) executed by the CPU 1100 when the computer 1000 is started, a program that depends on the hardware of the computer 1000, or the like.

The HDD 1400 is a recording medium that is readable by the computer, in which a program executed by the CPU 1100, data used by the program, or the like, is non-temporarily recorded. Specifically, the HDD 1400 is a recording medium in which the information processing program according to the present disclosure, which is an example of program data 1450, is recorded.

The communication interface 1500 is an interface for the computer 1000 to be connected to an external network 1550 (for example, the Internet). For example, the CPU 1100 receives data from another equipment or transmits data generated by the CPU 1100 to another equipment via the communication interface 1500.

The input/output interface 1600 is an interface for connecting an input/output device 1650 and the computer 1000 to each other. For example, the CPU 1100 receives data from an input device such as a keyboard or mouse via the input/output interface 1600. Further, the CPU 1100 transmits data to an output device such as a display, a speaker, or a printer via the input/output interface 1600. Further, the input/output interface 1600 may function as a medium interface for reading a program or the like recorded in a predetermined recording medium. Examples of the medium include an optical recording medium such as a digital versatile disc (DVD), a magneto-optical recording medium such as a magneto-optical disk (MO), a tape medium, a magnetic recording medium, and a semiconductor memory.

For example, in a case where the computer 1000 functions as the video processing device, the CPU 1100 of the computer 1000 implements the function of each component of the video processing device by executing the program loaded on the RAM 1200. In addition, the HDD 1400 stores the program according to the present disclosure and data in the video processing device and the recording device 40. The CPU 1100 reads the program data 1450 from the HDD 1400 and executes the program data 1450, but as another example, these programs may be acquired from another device via the external network 1550.

Supplementary Note

Note that the present technology can also have the following configurations.

(1)
An information processing device comprising:
    a target composition calculation unit that calculates a target composition based on a state of a subject; and
    a composition transition determination unit that switches a transition mode for transition to the target composition between a smooth composition transition mode in which the composition gradually transitions to the target composition and an instantaneous composition transition mode in which the composition instantaneously transitions to the target composition based on a situation of a change in the state.

(2)
The information processing device according to (1), wherein
    the state of the subject includes a state related to at least one of a movement direction of the subject, an orientation of the subject, or a size of the subject, and
    the situation of the change in state includes a situation related to at least one of a speed at which the movement direction is switched, a speed at which the orientation is switched, and a change in size of the subject.

(3)

The information processing device according to (1) or (2), wherein
the composition transition determination unit makes a change rate of a size of an angle of view immediately after the transition mode is switched from the smooth composition transition mode to the instantaneous composition transition mode different from a change rate of the size of the angle of view immediately before the transition mode is switched.

(4)

The information processing device according to any one of (1) to (3), wherein
the composition transition determination unit switches the transition mode to the instantaneous composition transition mode in a case where a new target composition is determined while the composition transitions in the smooth composition transition mode.

(5)

The information processing device according to any one of (1) to (3), wherein
the composition transition determination unit switches the transition mode to the instantaneous composition transition mode in a case where the state greatly changes beyond an allowable criterion while the composition transitions in the smooth composition transition mode.

(6)

The information processing device according to any one of (1) to (5), wherein
the composition transition determination unit prohibits selection of the instantaneous composition transition mode for a predetermined period after the instantaneous composition transition mode is selected.

(7)

The information processing device according to any one of (1) to (6), wherein
the state of the subject is acquired by performing image analysis on a captured video of the subject.

(8)

The information processing device according to any one of (1) to (6), wherein
the state of the subject is acquired based on sensor position information of a position sensor attached to the subject.

(9)

The information processing device according to any one of (1) to (8), further comprising:
a video selection unit that selects one captured video corresponding to the state of the subject from among a plurality of captured videos of the subject captured from different viewpoints; and
a video switching unit that outputs a video area clipped from the selected captured video as a framing video.

(10)

The information processing device according to (9), wherein
the video selection unit prohibits selection of another captured video for a predetermined period after one of the captured videos is selected.

(11)

The information processing device according to (10), wherein
the video selection unit makes a change rate of a size of an angle of view immediately after another captured video is selected different from a change rate of the size of the angle of view immediately before another captured video is selected.

(12)

The information processing device according to any one of (1) to (11), further comprising
an object recognition unit that detects an object to be a basis of calculation of the target composition together with the subject from a captured video of the subject.

(13)

The information processing device according to any one of (1) to (12), further comprising
a camera control unit that controls a visual field of a camera that images the subject based on the state of the subject.

(14)

The information processing device according to (13), wherein
the camera control unit presents recommendation information to a user who images the subject based on a difference between a visual field of a current frame and a target visual field.

(15)

The information processing device according to any one of (9) to (11), further comprising
a camera control unit that calculates a visual field of a camera that has captured an unselected captured video based on an angle of view of the video area clipped from the selected captured video.

(16)

An information processing method executed by a computer, the information processing method comprising:
calculating a target composition based on a state of a subject; and
switching a transition mode for transition to the target composition between a smooth composition transition mode in which the composition gradually transitions to the target composition and an instantaneous composition transition mode in which the composition instantaneously transitions to the target composition based on a situation of a change in the state.

(17)

A program for causing a computer to implement:
calculating a target composition based on a state of a subject; and
switching a transition mode for transition to the target composition between a smooth composition transition mode in which the composition gradually transitions to the target composition and an instantaneous composition transition mode in which the composition instantaneously transitions to the target composition based on a situation of a change in the state.

REFERENCE SIGNS LIST 10, 50, 60, 80, 90 VIDEO PROCESSING DEVICE (INFORMATION PROCESSING DEVICE)
20 CAMERA
16 TARGET COMPOSITION CALCULATION UNIT
17 COMPOSITION TRANSITION DETERMINATION UNIT
71 VIDEO SELECTION UNIT
72 VIDEO SWITCHING UNIT
81 OBJECT RECOGNITION UNIT
91 CAMERA CONTROL UNIT
1000 COMPUTER
1450 PROGRAM DATA (PROGRAM)
AV ANGLE OF VIEW
CP COMPOSITION
CV CAPTURED VIDEO

OB OBJECT
OV FRAMING VIDEO
POI SENSOR POSITION INFORMATION
SE POSITION SENSOR
SU SUBJECT
TCP TARGET COMPOSITION

The invention claimed is:

1. An information processing device comprising:
a target composition calculation unit that calculates a target composition based on a state of a subject; and
a composition transition determination unit that switches a transition mode for transition to the target composition between a smooth composition transition mode in which the composition gradually transitions to the target composition and an instantaneous composition transition mode in which the composition instantaneously transitions to the target composition based on a situation of a change in the state.

2. The information processing device according to claim 1, wherein
the state of the subject includes a state related to at least one of a movement direction of the subject, an orientation of the subject, or a size of the subject, and
the situation of the change in state includes a situation related to at least one of a speed at which the movement direction is switched, a speed at which the orientation is switched, and a change in size of the subject.

3. The information processing device according to claim 1, wherein
the composition transition determination unit makes a change rate of a size of an angle of view immediately after the transition mode is switched from the smooth composition transition mode to the instantaneous composition transition mode different from a change rate of the size of the angle of view immediately before the transition mode is switched.

4. The information processing device according to claim 1, wherein
the composition transition determination unit switches the transition mode to the instantaneous composition transition mode in a case where a new target composition is determined while the composition transitions in the smooth composition transition mode.

5. The information processing device according to claim 1, wherein
the composition transition determination unit switches the transition mode to the instantaneous composition transition mode in a case where the state greatly changes beyond an allowable criterion while the composition transitions in the smooth composition transition mode.

6. The information processing device according to claim 1, wherein
the composition transition determination unit prohibits selection of the instantaneous composition transition mode for a predetermined period after the instantaneous composition transition mode is selected.

7. The information processing device according to claim 1, wherein
the state of the subject is acquired by performing image analysis on a captured video of the subject.

8. The information processing device according to claim 1, wherein
the state of the subject is acquired based on sensor position information of a position sensor attached to the subject.

9. The information processing device according to claim 1, further comprising:
a video selection unit that selects one captured video corresponding to the state of the subject from among a plurality of captured videos of the subject captured from different viewpoints; and
a video switching unit that outputs a video area clipped from the selected captured video as a framing video.

10. The information processing device according to claim 9, wherein
the video selection unit prohibits selection of another captured video for a predetermined period after one of the captured videos is selected.

11. The information processing device according to claim 10, wherein
the video selection unit makes a change rate of a size of an angle of view immediately after another captured video is selected different from a change rate of the size of the angle of view immediately before another captured video is selected.

12. The information processing device according to claim 9, further comprising
a camera control unit that calculates a visual field of a camera that has captured an unselected captured video based on an angle of view of the video area clipped from the selected captured video.

13. The information processing device according to claim 1, further comprising
an object recognition unit that detects an object to be a basis of calculation of the target composition together with the subject from a captured video of the subject.

14. The information processing device according to claim 1, further comprising
a camera control unit that controls a visual field of a camera that images the subject based on the state of the subject.

15. The information processing device according to claim 14, wherein
the camera control unit presents recommendation information to a user who images the subject based on a difference between a visual field of a current frame and a target visual field.

16. An information processing method executed by a computer, the information processing method comprising:
calculating a target composition based on a state of a subject; and
switching a transition mode for transition to the target composition between a smooth composition transition mode in which the composition gradually transitions to the target composition and an instantaneous composition transition mode in which the composition instantaneously transitions to the target composition based on a situation of a change in the state.

17. A program for causing a computer to implement:
calculating a target composition based on a state of a subject; and
switching a transition mode for transition to the target composition between a smooth composition transition mode in which the composition gradually transitions to the target composition and an instantaneous composition transition mode in which the composition instantaneously transitions to the target composition based on a situation of a change in the state.

* * * * *